(12) United States Patent
Sadiq et al.

(10) Patent No.: US 9,657,268 B2
(45) Date of Patent: *May 23, 2017

(54) BONE MARROW-DERIVED MESENCHYMAL STEM CELLS AS A SOURCE OF NEURAL PROGENITORS

(71) Applicant: MULTIPLE SCLEROSIS RESEARCH CENTER OF NEW YORK, New York, NY (US)

(72) Inventors: Saud A. Sadiq, Franklin Lakes, NJ (US); Violaine K. Harris, New York, NY (US)

(73) Assignee: MULTIPLE SCLEROSIS RESEARCH CENTER OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/525,919

(22) Filed: Oct. 28, 2014

(65) Prior Publication Data

US 2015/0064145 A1    Mar. 5, 2015

Related U.S. Application Data

(63) Continuation of application No. 14/139,152, filed on Dec. 23, 2013, which is a continuation of application No. 12/377,900, filed as application No. PCT/US2007/023184 on Nov. 2, 2007, now Pat. No. 8,642,331.

(60) Provisional application No. 60/856,515, filed on Nov. 3, 2006.

(51) Int. Cl.
| | |
|---|---|
| C12N 5/0775 | (2010.01) |
| C12N 5/079 | (2010.01) |
| C12N 5/0797 | (2010.01) |
| A61K 35/30 | (2015.01) |
| C12N 5/0793 | (2010.01) |

(52) U.S. Cl.
CPC ............ *C12N 5/0622* (2013.01); *A61K 35/30* (2013.01); *C12N 5/0619* (2013.01); *C12N 5/0623* (2013.01); *C12N 5/0663* (2013.01); *C12N 2501/00* (2013.01); *C12N 2501/11* (2013.01); *C12N 2501/115* (2013.01); *C12N 2501/13* (2013.01); *C12N 2502/08* (2013.01); *C12N 2506/1353* (2013.01)

(58) Field of Classification Search
None
See application file for complete search history.

(56) References Cited

U.S. PATENT DOCUMENTS

| | | | |
|---|---|---|---|
| 7,037,719 B1 | 5/2006 | Buck et al. | |
| 8,017,112 B2 * | 9/2011 | Li et al. | 424/93.7 |
| 2004/0208858 A1 | 10/2004 | Tennekoon et al. | |
| 2004/0259254 A1 | 12/2004 | Honmou et al. | |
| 2006/0275272 A1 * | 12/2006 | Li et al. | 424/93.7 |

FOREIGN PATENT DOCUMENTS

| | | |
|---|---|---|
| WO | WO 2006/134602 A2 | 12/2005 |
| WO | 2008057443 A2 | 5/2008 |

OTHER PUBLICATIONS

Mareschi et al., Exp Hematol., 34(11):1563-1572, Nov. 2006.*
Mazzini et al., ALS and other motor neuron disorders, vol. 4: 158-161, 2003.*
Mohyeddin Bonab et al., Iran J Immunol., 4(1):50-57, 2007.*
Bossolasco et al., Exp. Neurol., 193:312-325, 2005.*
Harris et al., Stem Cells Translational Medicine, 1:536-547, 2012.*
Maric and Barker 2004, Molecular Neurobiology 30(1):49-76.*
Clinical Trials identifier NCT00395200, Nov. 1, 2006 [online] Retrieved from <https://www.clinicaltrials.gov/ct2/show/NCT00395200?term=NCT00395200&rank=1>; Retrieved on Apr. 19, 2016.*
Mohyeddin Bonab et al. Iran J Immunol. 4(1):50-57, Mar. 2007.*
Oka et al., Brain Research, 1030:94-102, 2004.*
Kobayashi et al., J Bone and Joint Surgery, 87B:1426-1433 (May 2005).*
Zappia E. et al., "Mesenchymal stem cells ameliorate experimental autoimmune encephalomyelitis inducing T-cell anergy", Blood 106(5): 1755-1761 (2005).
Zhang J. et al., "Human bone marrow stromal cell treatment improves neurological functional recovery in EAE mice", Experimental Neurology 195: 16-26 (2005).
Gerdoni E. et al., "Mesenchymal Stem Cells Effectively Modulate Pathogenic Immune Response in Experimental Autoimmune Encephalomyelitis", Ann Neurol 61: 219-227 (2007).
Bartholomew A. et al., "Mesenchymal stem cells suppress lymphocyte proliferation in vitro and prolong skin graft survival in vivo", Experimental Hematology 30: 42-48 (2002).
Koc O. N. et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy", Journal of Clinical Oncology 18(2): 307-316 (2000).
Corti S. et al., "Wild-type bone marrow cells ameliorate the phenotype of SOD1-G93A ALS mice and contribute to CNS, heart and skeletal muscle tissues", Brain 127: 2518-2532 (2004).

(Continued)

*Primary Examiner* — Kimberly A. Ballard
*Assistant Examiner* — Stacey N MacFarlane
(74) *Attorney, Agent, or Firm* — Scully Scott Murphy & Presser

(57) ABSTRACT

Methods are provided for treating and/or reducing the severity of multiple sclerosis in a human, by administering autologous mesenchymal stem cell-derived neural precursors. Also described is an in vitro method for differentiating mesenchymal stem-cell derived neural precursor oligodendroglial and neuronal cell types.

11 Claims, 8 Drawing Sheets

(56) References Cited

OTHER PUBLICATIONS

Patrikios P. et al., "Remyelination is extensive in a subset of multiple sclerosis patients", Brain 127: 3165-3172 (2006).
Bakshi A. et al., "Lumbar Puncture Delivery of Bone Marrow Stromal Cells in Spinal Cord Contusion: A Novel Method for Minimally Invasive cell Transplantation", Journal of Neurotrauma 23(1): 55-65 (2006).
Lepore A. C. et al., "Neural precursor cells can be delivered into the injured cervical spinal cord by intrathecal injection at the lumbar cord", Brain Research 1045: 206-216 (2005).
Johanson C. E. et al., "Enhanced Prospects for Drug Delivery and Brain Targeting by the Choroid Plexus-CSF Route", Pharmaceutical Research 22(7): 1011-1037 (2005).
Sadiq S. A. et al., "Long-term intrathecal baclofen therapy in ambulatory patients with spasticity", J Neurol 253: 563-569 (2006).
Arnhold S. et al., "Human bone marrow stroma cells display certain neural characteristics and integrate in the subventricular compartment after injection into the liquor system", European Journal of Cell Biology 85: 551-565 (2006).
Chen J. et al., "Therapeutic benefit of intracerebral transplantation of bone marrow stromal cells after cerebral ischemia in rats", Journal of the Neurological Sciences 189: 49-57 (2001).
Mannello F. et al., "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Enriched Plasma; Serum-Free, Serum Replacement Nonconditioned Medium, or Ad Hoc Formula All That Glitters Is Not Gold!", Stem Cells 25: 1603-1609 (2007).
Garin T. et al., "CD44 variant DNA vaccination with virtual lymph node ameliorates experimental autoimmune encephalomyelitis through the induction of apoptosis", Journal of the Neurological Sciences 258: 17-26 (2007).
Prockop D. J. et al., "One strategy for cell and gene therapy: Harnessing the power of adult stem cells to repair tissues", PNAS 100(Suppl 1): 11917-11923 (2003).
Dominici M. et al., "Minimal criteria for defining multipotent mesenchymal stromal cells. The International Society for Cellular Therapy position statement", Cytotherapy 8(4): 315-317 (2006).
Black I. B. et al., "Adult Rat and Human Bone Marrow Stromal Stem Cells Differentiate into Neurons", Blood Cells, Molecules, and Diseases 27(3): 632-636 (2001).
Keilhoff, G. et al., "Transdifferentiation of Mesenchymal Stem Cells into Schwann Cell-Like Myelinating Cells" European Journal of cell Biology (2006) pp. 11-24, vol. 85(1).
Padovan, C.S. et al., "Expression of Neuronal Markers in Differentiated Marrow Stromal Cells and CD133+ Stem-Like Cells" Cell Transplantation (2003) pp. 839-848, vol. 12(8).
Wislet-Gendebien, S. et al., "Astrocytic and Neuronal Fate of Mesenchymal Stem Cells Expressing Nestin" Brain Research Bulletin (2005) pp. 95-102, vol. 68(1-2).
Martino, G. et al., "The Therapeutic Potential of Neural Stem Cells" Nature Reviews: Neuroscience (2006) pp. 395-406, vol. 7(5).
Karussis, D. et al., "Neuroprotection in Multiple Sclerosis" Clinical Neurology and Neurosurgery (2006) pp. 250-254, vol. 108(3).
Papadaki, HA et al., "Normal bone marrow hematopoietic stem cell reserves and normal stromal cell function support the use of autologous stem cell transplantation in patients with multiple sclerosis" Bone Marrow Transplantation 36: 1053-1063, 2005.
Stute, N. et al., "Autologous Serum for Isolation and Expansion of Human Mesenchymal Stem Cells for Clinical Use", Experimental Hematology 32 pp. 1212-1225 (2004).
Kobayashi, T. et al., "Motility and Growth of Human Bone-Marrow Mesenchymal Stem Cells During Ex Vivo Expansion in Autologous Serum", J. Bone Joint Surg (Br) 87-B pp. 1426-1433 (2005).
Shahdadfar A., et al., "In Vitro Expansion of Human Mesenchymal Stem Cells: Choice of Serum is a Determinant of Cell Proliferation, Differentiation, Gene Expression, and Transcriptome Stability", Stem Cells, 23 pp. 1357-1366 (2005).
Porat, Y., et al., "Isolation of an adult blood-derived progenitor cell population capable of differentiation into angiogenic, myocardial and neural lineages", J. Haematology, vol. 135 pp. 703-714 Dec. 2006 (Article first published online: Oct. 16, 2006).
Kinner, et al., "Regulation of Smooth Muscle Actin Expression and Contraction in Adult Human Mesenchymal Stem Cells"; Experimental Cell Research 278, pp. 72-83, 2002.
Kohyama J., et al., "Brain from bone: Efficient "meta-differentiation" of marrow stroma-derived mature osteoblasts to neurons with NOggin or a demethylating agent"; Differentiation: Research in Biological Diversity; 2001; 68:235-244.
Peng, H., et al., "HIV-1-Infected and/or Immune Activated Macrophages Regulate Astrocyte SDF-1 Production Through IL-1β", NIH Public Access Author Manuscript, 1-4, published in final edited form as: Gila, Nov. 1, 2006; 54(6): 619-629.
Phillips, H. S., et al., "Molecular subclasses of high-grade glioma predict prognosis, delineate a pattern of disease progression, and resemble stages in neurogenesis", Cancer Cell 9:157-173 (Mar. 2006).
Sheen, V. L., et al., "Impaired Proliferation and Migration in Human Miller-Dieker Neural Precursors", Ann. Neurol. 60:137-144 (2006).
Singh, S. K. et al., "Identification of a Cancer Stem Cell in Human Brain Tumors", Cancer Research, 63:5821-2852, (Sep. 15, 2003).
Long, et al. "Neural Cell Differentiation In Vitro from Adult Human Bone Marrow Mesenchymal Stem Cells"; Stem Cells and Development. Feb. 2005, vol. 14, No. 1: 65-69.
Tyndall A., "Hematopoietic Stem Cell Transplantation in Rheumatic Diseases Other Than Systemic Sclerosis and Systemic Lupus Erythematosus", J Rheumatol 24 (Suppl 48): 94-97 (1997).
Ikehara S., "Bone Marrow Transplantation: A New Strategy for Intractable Diseases", Drugs of Today 38(2): 103-111 (2002).
Karussis D. et al., "Hematopoietic stem cell transplantation in multiple sclerosis: experimental evidence to rethink the procedures", Journal of the Neurological Sciences 223: 59-64 (2004).
Ferrari G. et al., "Muscle Regeneration by Bone Marrow-Derived Myogenic Progenitors", Science 279: 1528-1530 (1998).
Pittenger M. F. et al., "Multilineage Potential of Adult Human Mesenchymal Stem Cells", Science 284: 143-147 (1999).
Prockop D. J., "Marrow Stromal Cells as Stem Cells for Nonhematopoietic Tissues", Science 276: 71-74 (1997).
Woodbury D. et al., "Adult Bone Marrow Stromal Stem Cells Express Germline, Ectodermal, Endodermal, and Mesodermal Genes Prior to Neurogenesis", Journal of Neuroscience Research 96: 908-917 (2002).
Deng W. et al., "In Vitro Differentiation of Human Marrow Stromal Cells into Early Progenitors of Neural Cells by Conditions That Increase Intracellular Cyclic AMP", Biochemical and Biophysical Research Communications 282: 148-152 (2001).
Hermann A. et al., "Efficient generation of neural stem cell-like cells from adult human bone marrow stromal cells", Journal of Cell Science 117: 4411-4422 (2004).
Sanchez-Ramos J. et al., "Adult Bone Marrow Stromal Cells Differentiate into Neural Cells in Vitro", Experimental Neurology 164: 247-256 (2000).
Suzuki H. et al., "Neurospheres induced from bone marrow stromal cells are multipotent for differentiation into neuron, astrocyte, and oligodendrocyte phenotypes", Biochemical and Biophysical Research Communications 322: 918-922 (2004).
Woodbury D. et al., "Adult Rat and Human Bone marrow Stromal cells Differentiate Into Neurons", Journal of Neuroscience Research 61: 364-370 (2000).
Nauta A. J. et al., "Immunomodulatory properties of mesenchymal stromal cells" Blood 110: 3499-3506 (2007).
Bai L. et al., "Human Mesenchymal Stem Cells Signals Regulate Neural Stem Cell Fate", Neurochem Res 32: 353-362 (2007).
Rivera F. J. et al., "Mesenchymal Stem Cells Instruct Oligodendrogenic Fate Decision on Adult Neural Stem Cells", Stem Cells 24: 2209-2219 (2006).
Hermann A. et al., "Comparative Analysis of Neuroectodermal Differentiation Capacity of Human Bone Marrow Stromal Cells Using Various Conversion Protocols", Journal of Neuroscience Research 83: 1502-1514 (2006).
Mareschi K. et al., "Neural differentiation of human mesenchymal stem cells: evidence for expression of neural markers and eag K+ channel types", Experimental Hematology 34: 1563-1572 (2006).

(56) References Cited

OTHER PUBLICATIONS

Lazarus H. M. et al., "Cotransplantation of HLA-Identical Sibling Culture-Expanded Mesenchymal Stem Cells and Hematopoietic Stem Cells in Hematologic Malignancy Patients", Biology of Blood and Marrow Transplantation 11: 389-398 (2005).
Le Blanc K. et al., "Immunobiology of Human Mesenchymal Stem Cells and Future Use in Hematopoietic Stem Cell Transplantation", Biology of Blood and Marrow Transplantation 11: 321-334 (2005).
Le Blanc K. et al., "Treatment of severe acute graft-versus-host disease with third party haploidentical mesenchymal stem cells", Lancet 363: 1439-1441 (2004).
Giordano A. et al., "From the Laboratory Bench to the Patient's Bedside: An Update on Clinical Trials With Mesenchymal Stem Cells", J. Cell. Physiol. 211: 27-35 (2007).
Horwitz E. M. et al., "Isolated allogeneic bone marrow-derived mesenchymal cells engraft and stimulate growth in children with osteogenesis imperfect: Implications for cell therapy of bone", PNAS 99(13): 8932-8937 (2002).
Le Blanc K. et al., "Fetal Mesenchymal Stem-Cell engraftment in Bone after In Utero Transplantation in a Patient with Severe Osteogenesis Imperfecta", Transplantation 79: 1607-1614 (2005).
Chen Shao-Liang et al., "Effect on Left ventricular Function of Intracoronary Transplantation of Autologous Bone Marrow Mesenchymal Stem Cell in Patients With Acute Myocardial Infarction", Am J Cardiol 94: 92-95 (2004).
Katritsis D. et al., "Transcoronary Transplantation of Autologous Mesenchymal Stem Cells and Endothelial Progenitors Into Infarcted Human Myocardium", Catheterization and Cardiovascular Interventions 65: 321-329 (2005).
Bang O. Y. et al., "Autologous Mesenchymal Stem Cell Transplantation in Stroke Patients", Ann Neurol 57: 874-882 (2005).
Mazzini L. et al., "Stem cell therapy in amyotrophic lateral sclerosis: a methodological approach in humans", ALS and other motor neuron disorders 4: 158-161 (2003).
Mazzini L. et al., "Autologous mesenchymal stem cells: clinical applications in amyotrophic lateral sclerosis", Neurol Res 28: 523-526 (2006).
Mazzini L. et al., "Stem cell treatment in Amyotrophic Lateral Sclerosis", Journal of the Neurological Sciences 265: 78-83 (2008).
University of Cambridge, "Mesenchymal Stem Cells in Multiple Sclerosis (MSCIMS)", http://clinicaltrials.gov/ct/show/NCT00395200;jsessionid+F5A5DF2968E1567A594549F1CCE4B7EForder+14, Mar. 23, 2009.
Mohyeddin Bonab M. et al., "Does Mesenchymal Stem Cell Therapy Help Multiple Sclerosis Patients Report of a Pilot Study", Iran. J. Immunol. 4(1): 50-57 (2007).
Bertani N. et al., "Neurogenic potential of human mesenchymal stem cells revisited: analysis by immunostaining, time-lapse video and microarray", Journal of Cell Science 118: 3925-3936 (2005).
Neuhuber B. et al., "Reevaluation of In Vitro Differentiation Protocols for Bone Marrow Stromal Cells: Disruption of Actin Cytoskeleton Induces Rapid Morphological Changes and Mimics Neuronal Phenotype", Journal of Neuroscience Research 77: 192-204 (2004).
Wislet-Gendebien S. et al., "Regulation of neural markers nestin and GFAP expression by cultivated bone marrow stromal cells", Journal of Cell Science 116: 3295-3302 (2003).
Chopp M. et al., "Spinal cord injury in rat: treatment with bone marrow stromal cell transplantation", NeuroReport 11 (13): 3001-3005 (2000).
Hofstetter C. P. et al., "Marrow stromal cells form guiding strands in the injured spinal cord and promote recovery", PNAS 99(4): 2199-2204 (2002).
Ohta M. et al., "Bone marrow stromal cells infused into the cerebrospinal fluid promote functional recovery of the injured rat spinal cord with reduced cavity formation", Experimental Neurology 187: 266-278 (2004).
Satake K. et al., "Migration of Mesenchymal Stem Cells Through Cerebrospinal Fluid into Injured Spinal Cord Tissue", Spine 29: 1971-1979 (2004).
Zurita M. et al., "Functional recovery in chronic paraplegia after bone marrow stromal cells transplantation", NeuroReport 15(7): 1105-1108 (2004).
Zurita M. et al., "Bone marrow stromal cells can achieve cure of chronic paraplegic rats: Functional and morphological outcome one year after transplantation", Neuroscience Letters 402: 51-56 (2006).
Lu D. et al., "Neural and marrow-derived stromal cell sphere transplantation in a rat model of traumatic brain injury", J Neurosurg 97: 935-940 (2002).
Lu D. et al., "Intraarterial Administration of Marrow Stromal Cells in a Rat Model of Traumatic Brain Injury", Journal of Neurotrauma 18: 813-819 (2001).
Lu D. et al., "Adult bone marrow stromal cells administered intravenously to rats after traumatic brain injury migrate into brain and improve neurological outcome", NeuroReport 12(35): 559-563 (2001).
Bae Jae-Sung et al., "Bone Marrow-Derived Mesenchymal Stem Cells Promote Neuronal Networks with Functional Synaptic Transmission After Transplantation into Mice with Neurodegeneration", Stem Cells 25: 1307-1316 (2007).
Hellmann M. A. et al., "Increased survival and migration of engrafted mesenchymal bone marrow stem cells in 6-hydroxydopamine-lesioned rodents", Neuroscience Letters 395: 124-128 (2006).
Akiyama Y. et al., "Remyelination of the Rat Spinal Cord by Transplantation of Identified Bone Marrow Stromal Cells", The Journal of Neuroscience 22(15): 6623-6630 (2002).
Deng Y. B. et al., "Implantation of BM mesenchymal stem cells into injured spinal cord elicits de novo neurogenesis and functional recovery: evidence from a study in rhesus monkeys", Cytotherapy 8(3): 210-214 (2006).
Isakova I. A. et al., "Preclinical Evaluation of Adult Stem Cell Engraftment and Toxicity in the CNS of Rhesus Macaques", Molecular Therapy 13(6): 1173-1184 (2006).
Habisch H. J. et al., "Intrathecal application of neuroectodermally converted stem cells into a mouse model of ALS" limited intraparenchymal migration and survival narrows therapeutic effects, J. Neural Transm 114: 1395-1406 (2007).
Supplementary European Search Report dated Jul. 8, 2010 issued in European Patent Application No. EP 07 86 7379.
Communication dated May 19, 2011 in connection with European Patent Application No. 07867349.8.
http://findarticles.com/p/articles/mi_hb034/is_7_31/ai_n32043050/?tag=con . . . , "Primary Neuron Growth Medium" accessed Apr. 24, 2012.
Kabos, Peter, et al., "Generation of Neural Progenitor Cells From Whole Adult Bone Marrow", Experimental Neurology 178, pp. 228-293 (2002).
European Search Report dated May 2, 2016 received in corresponding European Patent Application No. 15195728.9.
Zappia, E. et al., "Mesenchymal stem cells ameliorate experimental autoimmune encephalomyelitis inducing T-cell energy", Blood (Sep. 1, 2005), vol. 106, No. 5, pp. 1755-1761.
Karussis, D. et al., "Neuroprotection in multiple sclerosis", Clinical Neurology and Neurosurgery, (Mar. 1, 2006), vol. 108, No. 3, pp. 250-254.
Extended European Search Report dated Aug. 12, 2016 issued in European Patent Application No. 15195728.9.

\* cited by examiner

BONE MARROW-DERIVED MESENCHYMAL STEM CELLS AS A SOURCE OF NEURAL PROGENITORS

CROSS REFERENCE TO RELATED APPLICATION

The present application is a continuation application of U.S. patent application Ser. No. 14/139,152, filed Dec. 23, 2013 which is a continuation application of U.S. patent application Ser. No. 12/377,900, filed Feb. 18, 2009, now U.S. Pat. No. 8,642,331, which is the national phase under §371 of International Application No. PCT/US07/023184, filed Nov. 2, 2007, which claims benefit of U.S. Provisional Patent Application No. 60/856,515, filed Nov. 3, 2006.

FIELD OF THE INVENTION

The present invention relates to the use of bone marrow-derived mesenchymal stem cells as a source of neural progenitors for use in autologous stem cell therapy of multiple sclerosis.

BACKGROUND

Multiple sclerosis (MS) is a chronic human autoimmune disease of the central nervous system (CNS) that affects 600,000 Americans and 2.5 million individuals worldwide. MS is most often diagnosed between the ages of 20 and 50 and is second only to trauma in causing neurological disability in young adults. The disease usually starts between 20 to 40 years of age and there are two major forms. Relapsing-remitting MS (RR-MS) is the most frequent form (85%-90%) and affects women about twice as often as men, Most RR-MS patients later develop the second major form known as secondary progressive MS (SP-MS). About 10%-15% of patients show a steady progression following disease onset with the absence of relapses, termed primary progressive PP-MS. (Sospedra, et al., *Annu Rev Immunol* 23, 683 [2005]), MS is a highly heterogeneous disease where every patient differs in clinical presentation and response to treatments.

Although the exact cause of MS is unknown, pathologically there is inflammation-induced destruction of the myelin sheath that surrounds axons in the brain and spinal cord leading to decreased nerve conduction. Clinically, the loss of myelin leads to a variety of neurological symptoms and, in some patients, major disability. In most patients with relapsing-remitting disease, inflammation-induced demyelination is spontaneously repaired by oligodendrocytes, the cells in the brain that produce and maintain myelin, Acute inflammation and chronic demyelination eventually lead to destruction of oligodendrocytes and axonal loss. The secondary progressive phase of MS is characterized by neurodegeneration and treatment-resistant functional deterioration.

Current treatment options for MS are immunomodulatory and immunosuppressive therapies that are mostly effective during the inflammation-mediated relapsing-remitting phase of MS. These therapies are only partially effective in slowing down the progressive phase of MS, which may be largely neurodegenerative. There is an urgent need for therapies that can stop or reverse the progression of MS through strategies involving neural repair and regeneration.

Stem cell therapies hold much promise for regenerative medicine. Stem cells have the potential to develop into many different cell types in the body. Stem cells can theoretically divide without limit to replenish cells in need of repair. There are different types of stem cells with varying ranges of commitment options. Embryonic stem cells hold great potential for regenerative medicine, however, they have a number of disadvantages including the possibility of transplant rejection and possible teratoma formation if the cells are not properly differentiated prior to transplantation. Adult stem cells such as neural stem cells (NSC) and oligodendrocyte precursor cells (OPC) have a more restricted developmental potential than embryonic stem cells and generally differentiate along their lineage of origin. While adult neural stem cells also represent a promising treatment option for neurodegenerative disorders, there are a number of disadvantages, including difficulty of isolation, limited expansion capability, and immune rejection of transplanted donor cells.

Bone marrow-derived mesenchymal stem cells (MSCs) are another type of adult stem cell that differentiates into non-hematopoietic tissues including osteoblasts, adipocytes, chondrocytes, and myoblasts (Ferrari, et. al., *Science* 279: 1528.1530 [1998]; Pittenger, et.al., *Science* 287:143-147 [1999]; Prockop, et. al., *Science* 276:71-74 [1997]).

The use of bone marrow-derived stem cells has many therapeutic advantages. Bone marrow is an easily accessible and autologous source of stem cells, thus eliminating the risk of rejection. Since mesenchymal stem cells have enormous ex vivo expansion capability, it is possible to expand a small population of cells into enough cells for clinical application.

MSCs have a number of remarkable in vitro characteristics, making them a very attractive candidate for neurodegenerative and immunological disorders.

MSCs exhibit differentiation plasticity, meaning that they are capable of differentiating along lineages other than their tissue of origin (Jiang, et. al., *Nature* 418:41-49 [2002]; Woodbury, et.al., *J. Neurosci Res* 69:908-917 [2002]). MSCs are capable of forming cells with neuronal and glial phenotypes in vitro (Black et.al., *Blood Cells Mol Dis* 27: 632-636 [2001]; Deng et.al., *Biochem Biophys Res Commun* 282: 148-152 [2001]; Hermann, et. al., *J. Cell Sci* 117:4411-4422 [2004]; Sanchez-Ramos, et. al., *Exp. Neurol* 164: 247-256 [2000]; Suzuki, et. al., *Biochem Biophys Res Commun* 322: 918-922 [2004]; Woobury , et. al., *J. Neurosci Res* 61; 364-370 [2000]). MSCs incubated in the presence of growth factors basic fibroblast growth factor (bFGF) and epidermal growth factor (EGF) displayed a neural stem cell morphology with increased expression of neural stem cell markers (Hermann, et. al., *J. Cell Sci* 117: 4411-4422 [2004]). These studies raise the possibility that MSCs may be capable of cell replacement in the damaged brain and spinal cord.

MSCs have an immunoregulatory function, It has been demonstrated that MSCs can suppress T, B, NK, and dendritic cell activation and proliferation (Uccelli, et. el., *Expert Opin Biol Ther* 6: 17-22 [2006]). These anti-inflammatory properties of MSCs suggest a possible clinical application for immune-mediated disease.

MSCs can promote the genesis of neurons and oligodendrocytes from neural stem cells (Bai, et. al., *Neurothem Res* 32: 353-362 [2007]; Rivera, et. al. *Stem Cell* 24; 2209-2219 [2006]). These recent studies show that MSCs secrete trophic factors that influence neural stem cell progeny, which may have clinical implications in enhancing recovery after a wide range of CNS injuries.

The findings that MSCs can generate neural stem cell-like cells that express neural stem cell markers (Hermann, et. al., *J Cell Sci* 117: 4411-4422 [2004]) suggest that MSC-derived neural precursors may be a more potent source for therapeutic use in the CNS. MSCs cultured in neural stem cell-specific media (serum free media containing 20 ng/ml of both EGF and bFGF) exhibited neurosphere morphology with an increase in neural stem cell marker genes (Nestin), glial genes (GFAP, MBP) and neuronal genes (Map2, Neurofilament, Tyrosine hydroxylase, voltage dependent K+ channels) (Hermann, et. al., *J Cell Sci* 117: 4411-4422 [2004]; Hermann, et. al., *J Neurosci Res* 83: 1502-1514 [2006]; Mareschi, et. al., *Exp Hematol* 34: 1563-1572 [2006]). In comparing different culture conditions to convert MSCs to neural precursors, one study found that MSCs cultured in Neural Progenitor Maintenance Media (NPMM, Lonza) acquired the morphological characteristics, neural markers, and electrophysiological properties suggestive of neural differentiation (Mareschi, et. al., *Exp Hematol* 34: 1563-1572 [2006]).

Use of Mesenchymal Stem Cells in Neurological Diseases

A number of clinical trials have analyzed the safety and therapeutic benefit of MSCs. Several hundred patients have been infused with allogeneic HLA-matched MSCs in the context of hematopoietic stem-cell transplant for malignancy or inborn metabolic disease (Lazarus, et. al., *Biol Blood Marrow Transplant* 11: 389-398 [2005]; Le Blanc, et. al., *Biol Blood Marrow Transplant* 11: 321-334 [2005]). Severe graft vs. host disease (GvHD) was reversed upon infusion of donor-derived MSCs (Le Blancet. al., *Lancet* 363: 1439-1441 [2004]). In these studies, infusion of approximately 1-2 million cells/kg MSCs is well tolerated with no side effects. Thus, initial clinical trial data suggests that MSC-based therapies hold much promise as immune modulators, and additional Phase 1/II trials studying the effects of the role of MSCs in the treatment of GvHD are ongoing (Giordano, et. al., *J Cell Physiol* 211: 27-35 [2007]). Furthermore, clinical trials examining MSCs in osteogenesis imperfecta (Horwitz, et. al., *Proc Natl Acad Sci USA* 99: 8932-8937 [2002]; Le Blanc, et. al., *Transplantation* 79: 1607-1614 [2005]), myocardial infarct (Chen, et. al., *Am J Cordial* 94; 92-95 [2004]; Katritsiset. al., *Catherter Cardiovas Intery* 65: 321-329 [2005]), and stroke (Bang, et. al., *Ann Neural* 57: 874-882 [2005]) have shown safety and efficacy for the treatment of these diseases as well.

In a recent clinical trial in Italy (Mazzini, et. al., *Amyotroph Lateral Scler Other Motor Neuron Disord* 4; 158-161 [2003]; Mazzini, et. al., *Neurol Res* 28: 523-526 [2006]; Mazzini, et. al., *Neural Sci* [2007]), autologous bone marrow-derived MSCs were transplanted directly into the spinal cord of nine patients with amyotrophic lateral sclerosis (ALS), a degenerative motor neuron disease. Intraspinal transplantation of an average of 32 million autologous MSCs was safe and well tolerated by ALS patients, within a follow-up period of 4 years. Minor adverse events were intercostal pain irradiation and leg sensory dysesthesia, which disappeared after 6 weeks, In 5 of the patients receiving autologous MSC transplantation, there was a significant slowing of the linear decline in the ALS-functional rating scale (Mazzini, et. al., *Neural Res* 28: 523-526 [2006]). Given the progressive nature of this disease, these findings suggest a clinical benefit of MSC transplantation and warrant further trials. The encouraging clinical results for autologous MSC transplantation in ALS and the safety and tolerability observed in the 4-year follow-up suggest that a similar approach could be taken to treat other neurodegenerative disorders such as MS.

Use of Mesenchymal Stem Cells in MS

Based on the preclinical data demonstrating peripheral immunosuppression in EAE, a current phase I/IIA research study is taking place at the University of Cambridge in Cambridge, England. The study aims to investigate the safety of intravenous administration of autologous MSCs in patients with multiple sclerosis. There are 20 patients enrolled in the study, and the dosage will be 2 million cells/kg (http://clinicaltrials.gov/ct/show/NCT00395200: jsessionid=F5A5DF2968E1567A594549F1CCE4B7EF? order=14).

In a recent pilot study conducted in Iran, human autologous MSCs were injected intrathecally in ten primary progressive and secondary progressive MS patients (Mohyeddin, et. al., *Iran J Immunol* 4: 50-57 [2007]). Researchers injected an average of 8.73 million cells. The highest dose was 13.2 million cells and the lowest dose was 2.5 million cells. Patients were followed for an average of nineteen months after treatment, with monthly follow-up exams and an MRI 12 months after intrathecal injection of autologous MSCs. Patients were evaluated for changes in EDSS score, changes in the number and size of lesions on an MRI, and subjective improvement. Researchers found that intrathecal autologous MSC transplantation was safe and well tolerated with side effects related to the intrathecal injection procedure (e.g. headache). Two patients contracted iatrogenic meningitis and both patients were treated successfully with antibiotics. They also noted that the therapy was associated with some improvement. One patient experienced a decrease in EDSS score. Four patients showed improvement in daily functions with no change in EDSS score. Five patients experienced an increase in EDSS score, and all five reported subjective improvement within three months of treatment. Researchers concluded that autologous intrathecal MSC injection is a safe and promising treatment for MS patients.

The use of MSC-derived neural precursors has not hereto before been reported for administration to humans.

SUMMARY OF THE INVENTION

The invention provides methods for the in vitro differentiation of mesenchymal stem cell-derived neural precursor cells. The invention further provides methods for treating and/or reducing the severity of multiple sclerosis in a human by administering mesenchymal stem cell-derived neural precursors to patient afflicted with multiple sclerosis.

The mesenchymal stem cell-derived neural precursor cells according to the present invention are formed by culturing the mesenchymal stem cells in a neural progenitor basal medium followed by plating the cells and culturing in basic fibroblast growth factor (bFGF). The neural precursor cells are then labeled, such as via fluorescent immunocytochemistry, for identification. The neural precursor cells include oligodendroglial and/or neuronal cells.

The administration of autologous mesenchymal stem cell-derived neural precursors to a patient includes the steps of: preparing an autologous growth serum obtained from the patient; collecting bone marrow derived stem cells from a patient to be treated by said method; isolating and expanding bone-marrow-derived mesenchymal stem cells in the growth serum; culturing and isolating mesenchymal stem cell-derived neural precursor cells from the mesenchymal stem cells; and intrathecally administering said autologous mesenchymal stem cell-derived neural precursors to said patient. The mesenchymal stem cell-derived neural precursors according to the present invention exhibit an increased amount of Nestin, neurofilament and GFAP (glial fibrillary acidic protein) markers and a decreased amount of Vimentin marker.

The above and other features of the invention, including various novel details of construction and combinations of parts, will now be more particularly described with reference to the accompanying drawings and pointed out in the claims. It will be understood that the particular devices and methods embodying the invention are shown by way of illustration only and not as a limitation of the invention. The principles and features of this invention may be employed in various and numerous embodiments without departing from the scope of the invention.

BRIEF DESCRIPTION OF THE FIGURES

These and other features, aspects, and advantages of the apparatus and methods of the present invention will become better understood with regard to the following description, appended claims, and accompanying drawings where:

Expression of β3-tubulin (neuronal marker) and O4 (early oligodendroglial differentiation marker) is significantly increased in MSC-NPs compared to MSCs when cultured in bFGF for 3 weeks.

Figure 2:
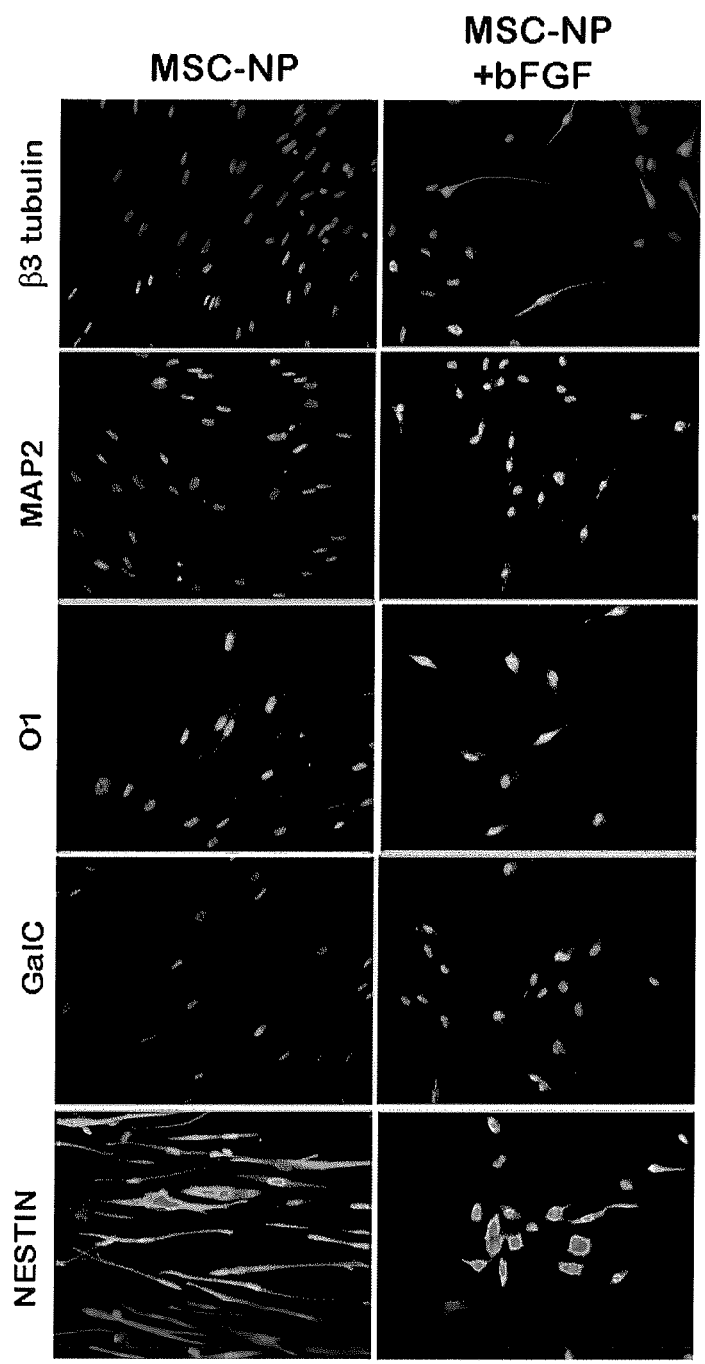

FIG. 2: Increased Neuronal and Oligodendroglial Marker Expression in MSC-Derived Neural Precursors after in vitro Differentiation.

Figure 3:
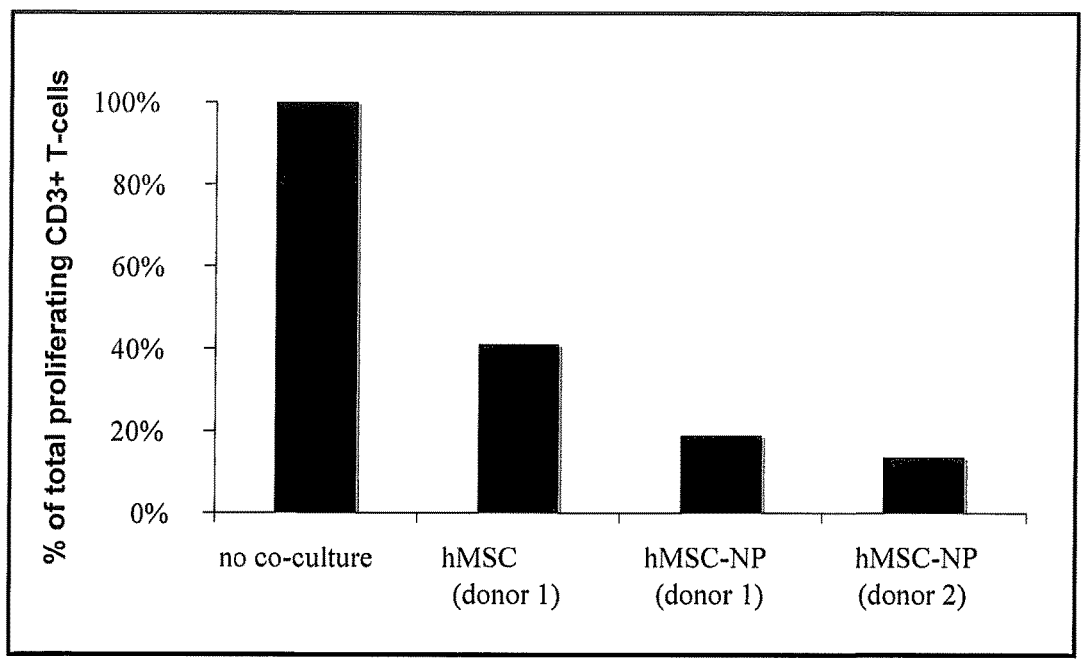

Neuronal markers (β3-tubulin and MAP-2) and oligodendroglia) markers (O1 and GalC) increase after 3 week differentiation in bFGF, Nestin expression, which is a neural progenitor marker, is decreased in approximately 50% of MSC-NPs after differentiation, FIG. 3 graphically illustrates that MSC-derived neural precursors display anti-inflammatory characteristics similar to MSCs via the inhibition of PHA-stimulated T-cell proliferation in a co-culture.

Figure 4:
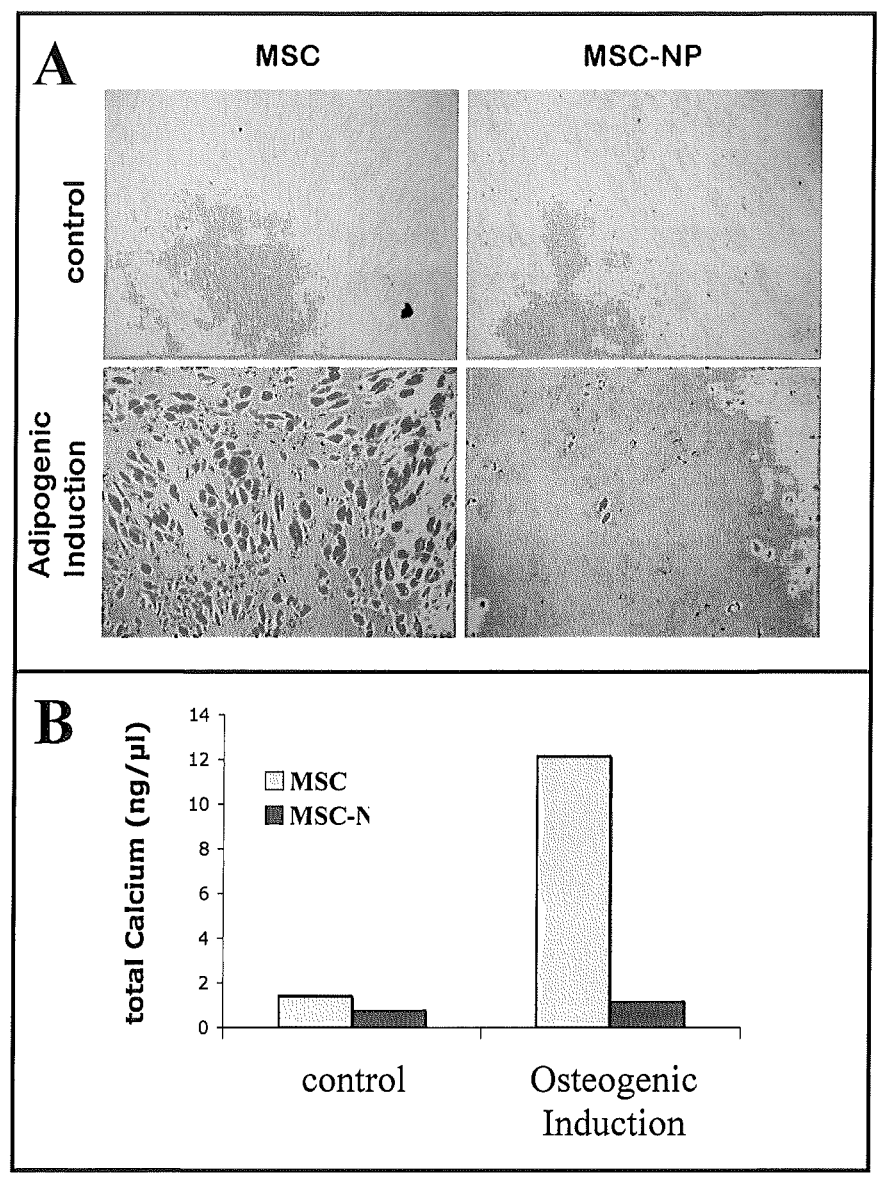

FIG. 4: MSC-Derived Neural Precursors (MSC-NP) Lose their Capacity to Differentiate into Mesodermal Lineages.

MSC-NPs show decreased ability to differentiate into Oil Red O positive adiopocytes (A) or calcium-containing osteocytes (B) compared to MSCs.

Figure 5:
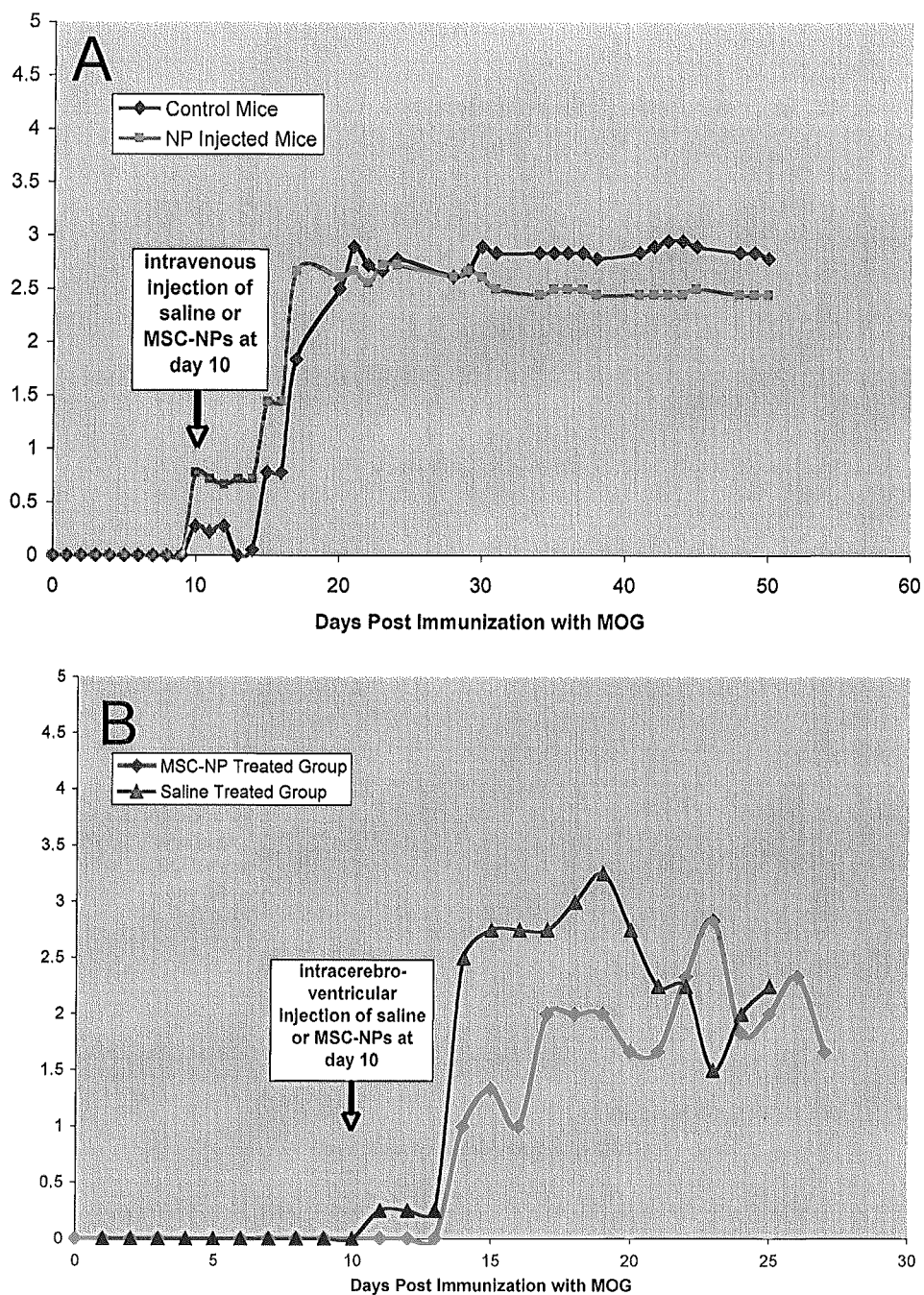

FIG. 5 graphically illustrates the decreased clinical score following intravenous (A) or intracerebroventricular (B) administration of mouse MSC-derived neural precursors at the time of EAE onset (day 10) in mice.

Figure 6:
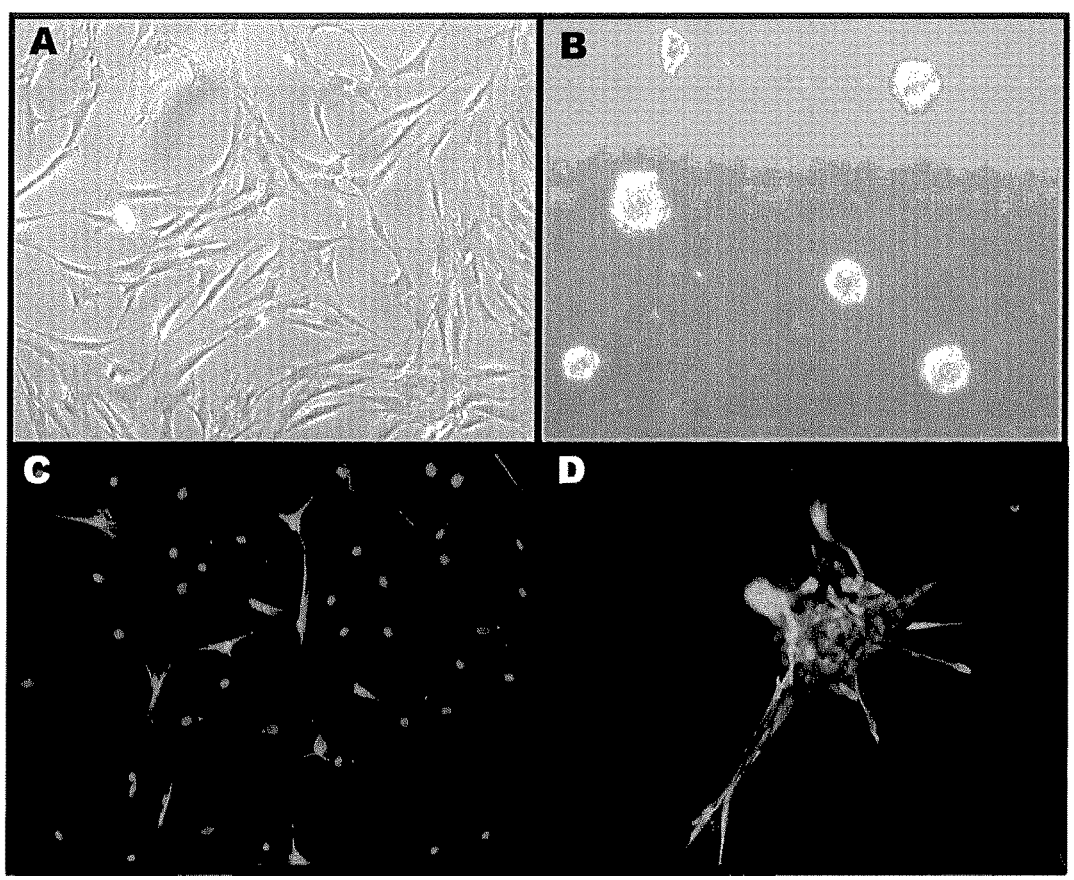

FIG. 6: Increased Nestin Expression in MSC-Derived Neural Precursors.

(A) Spindle-shaped morphology of human MSCs isolated from bone marrow and grown in MSCGM (mesecnchymal stem cell growth medium) (10% serum) as viewed by light microscopy, (B) Spherical morphology of MSC-derived neural precursors, Neural precursors were derived from MSCs after culturing in NPMM for 15 days. (C) Approximately 20% of human MSCs express Nestin protein. (D)>90% of MSC-derived neural precursors express Nestin protein. Nestin protein expression was determined by standard immunofluorescence, Cells were fixed in 4% paraformaldehyde and labeled with Nestin antibody (Chemicon) followed by anti-rabbit secondary antibody conjugated to Alexa-594 (Molecular Probes). Panels A-C were viewed at 100× magnification and panel D was viewed at 200× magnification.

Figure 7:
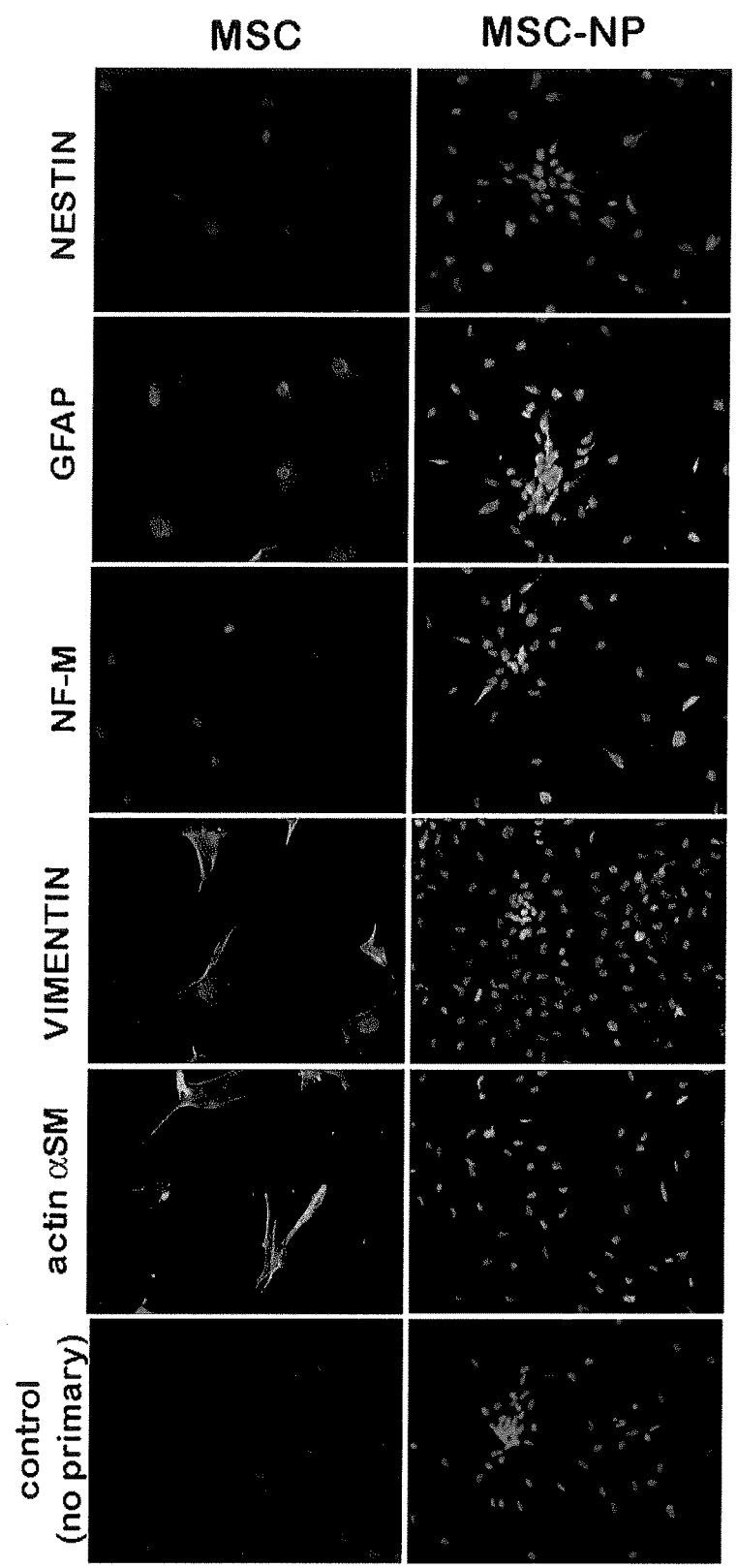

FIG. 7: MSC-Derived Neural Precursors (MSC-NP) show Increased Protein Expression of Nestin, GFAP and Neurofilament-M, and Decreased Expression of Vimentin and αSM actin compared to MSCs.

Figure 8:
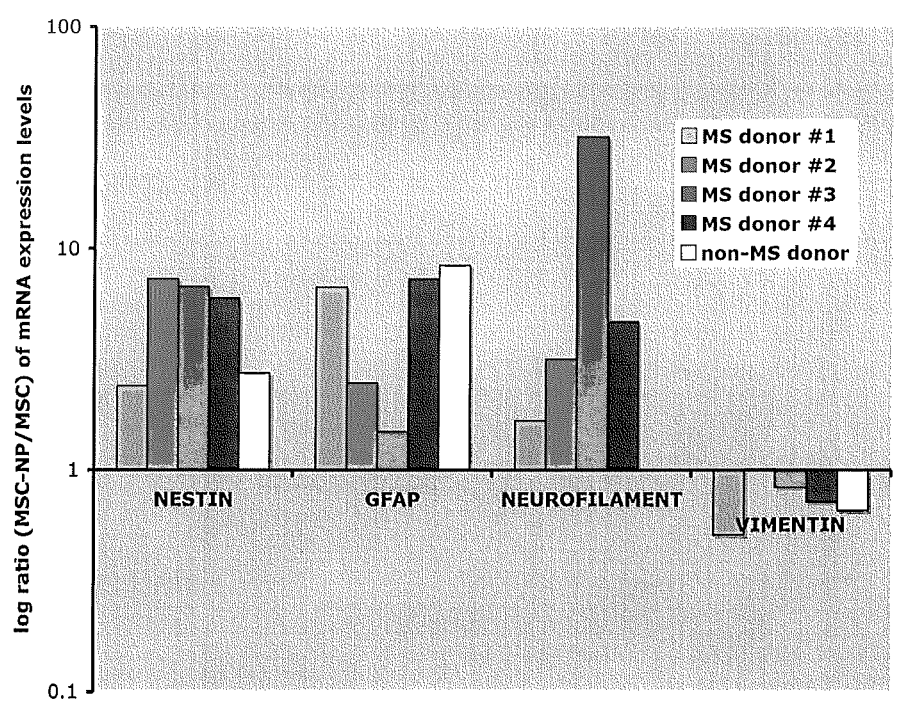

FIG. 8 graphically illustrates the increased protein expression in MSC-derived neural precursors of Nestin, GFAP and Neurofilament-M, and Decreased Expression of Vimentin and αSM actin compared to MSCs.

DETAILED DESCRIPTION

Multiple sclerosis patients typically experience progressive neurological decline due to prolonged autoimmune attack, failure of endogenous remyelinating mechanisms, and axonal loss. The use of autologous MSC-derived neural precursor cells is aimed at reversing the neurodegeneration that occurs in MS through repair and regeneration of damaged cells. Preclinical studies in animals demonstrate that MSC-based therapies have significant benefit in models of CNS injury and demyelinating disease. Clinical trial data has shown that MSC administration is safe and well tolerated, however MSC-derived neural precursor cells have not been used in clinical trials. Furthermore, clinical trials with MS and ALS patients suggest that MSCs may have some therapeutic benefit. The present invention is thus directed to elucidating the safety, tolerability, dosing and efficacy of intrathecal injections of autologous MSC-derived neural precursor cells in MS patients. This treatment could reverse neurodegeneration in demyelinating plaques in MS patients. Injections of MSC-derived neural precursor cells could also decrease the inflammatory response associated with MS attacks. Autologous MSC-derived neural precursor cell transplantation could serve as an effective template for neuroregeneration with minimal adverse side effects.

In vitro data suggests that pre-differentiation of MSCs into MSC-derived neural precursors is necessary for differentiation into a more mature neuronal or glial phenotype. While differentiation of MSCs directly into neuronal-like cells has been reported (Deng, et. al., *Biochem Blophys Res Commun* 282: 148-152 [2001]; Sanchez-Ramos, et. al., *Exp Neurol* 164: 247-256 [2000]; Woodbury, et. al., *J Neurosci Res* 61:364-370 [2000]), these changes are likely attributed to cellular toxicity (Bertani, et. al., *J Cell Sci* 118: 3925-3936 [2005]; Neuhuber, et. al, *J Neurosci Res* 77: 192-204 [2004]). Conversion of MSCs into MSC-derived neural precursors results in significantly increased Nestin expression (see e.g., FIG. 7), which is necessary for further differentiation into neurons and astrocytes (Wislet-Gendebien, et. al., *J Cell Sci* 116: 3295-3302).

Figure 1:
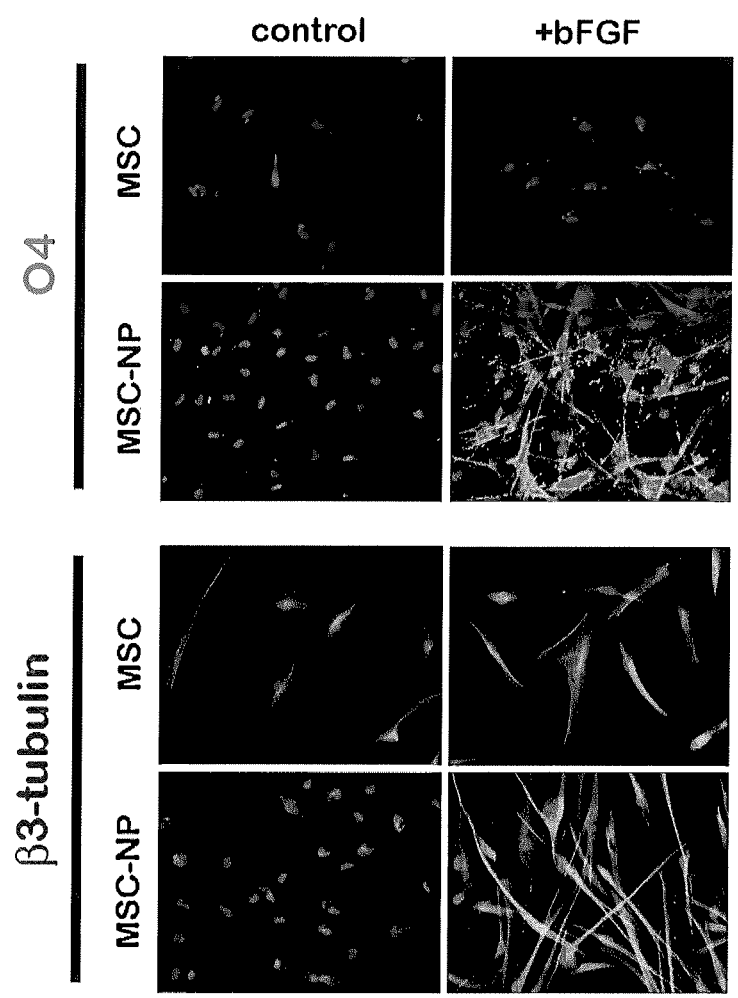
FIG. 1: Increased Neuronal and Oligodendroglial Marker Expression in MSC-Derived Neural Precursors (MSC-NP) and MSCs after in vitro Differentiation.

The inventors of the instant application have demonstrated that MSC-derived neural precursors, but not MSCs, are capable of in vitro differentiation into oligodendroglial (O4+) or neuronal (β3-Tubulin+) cell types (FIGS. 1 and 2). In addition, the present inventors have generated data that suggests that MSC-derived neural precursors retain the anti-inflammatory properties of MSCs (FIG. 3), but lose their differentiation plasticity (i.e. differentiation into osteoblasts or adipocytes) (FIG. 4).

These findings suggest that MSC-derived neural precursors are more likely to respond to differentiation cues in the CNS, and in addition can suppress the immune response and provide trophic support for damaged cells. Overall, these data support the rationale in this protocol to use MSC-derived neural precursors for cell-based therapy in multiple sclerosis.

The primary objective of the present invention was to determine the safety and effectiveness of using autologous mesenchymal stem cell-derived neural precursor cell therapies in MS. This was accomplished by performing intrathecal injections of isolated and expanded autologous MSC-derived neural precursor cells. Another objective is to determine the tolerability of dosing regimens of intrathecal administration of autologous mesenchymal stem cell-derived neural precursor cells over different time periods.

Studies in Animal Models of Neurological Diseases

A large number of studies have shown safe and effective transplantation of MSCs into preclinical animal models of CNS disease. In vivo studies examining spinal cord injury in rats have shown that transplanted MSCs effectively target the injured spinal cord tissue and support axonal growth promoting significant clinical recovery (Chopp, et. al., *Neuroreport* 11: 3001-3005 [2000]; Hofstetter, et. al., *Proc Natl Acad Sal USA* 99: 2199-2204 [2002]; Ohta, et. al., *Exp Neurol* 187: 226-278 [2004]; Satake, et. al., *Spine* 29: 1971-1979 [2004]; Zurita, *Neuroreport* 15: 1105-1108 [2004]; Zurita, *Neurosci Lett* 402: 51-56). In ischemic brain injury models in rats, transplanted MSCs migrated to the brain injury site and improved neurological outcome (Chen et. al., *Am J Cardiol* 94: 92-95 [2004]; Lu, et. al., *J Neurosurg* 97: 935-940 [2002]; Lu, et. al., *J Neurotrauma* 18: 813-819 [2001]; Lu, et. al., *Neuroreport* 12: 559-563 [2001]). Transplantation of MSCs into multiple other models of neurodegenerative disease have also shown effective survival, migration, and promotion of neural networks (Bae, et. al., *Stem Cells* 25: 1308-1316 [2007]; Hellmann, et. al., *Neurosci Lett* 395: 124-128 [2006]), demonstrating the neuroprotective and neuroregenerative properties of MSCs in rodent models. Furthermore, MSCs were capable of functional remyelination when transplanted into a demyelinated spinal cord (Akiyama, et. al., *J Neurosci* 22: 6623-6630 [2002]). In non-human primate models, preclinical evaluation of MSC implantation into the CNS of rhesus monkeys has shown cell engraftment, survival, homing to sites of injury, and neurological benefit with no toxicity (Deng, et. al., *Cytolherapy* 8: 210-214 [2006]; Isakova, et.al., *Mol Ther* 13: 1173-1184 [2006]), suggesting that MSC-based therapies represent a safe therapeutic approach for CNS disorders.

More limited preclinical data exists for MSC-derived neural precursors in the CNS. In a recent study 100,000 MSCs or MSC-derived neural precursors were transplanted intrathecally into the cisterna magna of a mouse model of ALS (Habisch, et. al., *J Neural Transm* (in press) [2007]). The primary outcome parameter was the effect on survival time, while secondary outcome measures included improvement of motor function and subarachnoidai and intraparenchymal cell distribution. Intrathecal transplantation of MSCs or MSC-derived neural precursors had no effect on survival times in the ALS mice compared to untreated mice, probably due to the lack of cell migration into the spinal cord.

Interestingly, there was a significant increase in pre-symptomatic motor performance in mice receiving MSCs or MSC-derived neural precursors. There was a widespread distribution of all transplanted cells within the subarachnoidal space, as well as significant intraparenchymal migration. This study demonstrated that MSC-derived neural precursors are tolerated as well as MSCs, and they show similar survival and migration characteristics in the CNS.

Studies in Animal Models of MS

MSC administration has also been tested in mice with experimental autoimmune encephalomyelitis (EAE), an experimental model for human multiple sclerosis. Experimental Autoimmune Encephalomyelitis (LAE), also called Experimental Allergic Encephalomyelitis, is an animal model of Multiple Sclerosis. Animal models of human diseases are diseases of non-human species (often rodents) which closely resemble their human counterparts and can be studied with a view to better understanding and treating the human form. LAE is not multiple sclerosis, nor is it a single disease in a single species, but its different forms resemble the various forms and stages of MS very closely in a large number of ways.

EAE is an acute or chronic-relapsing, acquired, inflammatory and deymyelinating autoimmune disease of the CNS, The animals are injected with the whole or parts of various proteins that make up myelin, the insulating sheath that surrounds nerve cells (neurons). These proteins induce an autoimmune response in the animals—that is the animal's immune system mounts an attack on its own myelin as a result of exposure to the injection. The animals develop a disease that shows pathological and clinical similarities to MS in humans.

EAE has been induced in a number of different animal species including mice, rats, guinea pigs, rabbits, macaques, rhesus monkeys and marmosets. For various reasons including the number of immunological tools, the availability, lifespan and fecundity of the animals and the resemblance of the induced disease to MS, mice and rats are the most commonly used species.

The animals are in-bred to reliably produce susceptibility to EAE in the animals. As with humans and MS, not all mice or rats will have a natural propensity to acquire EAE. Moreover, different breeds will develop different forms of EAE, some of which act as good models for the different human forms of MS. Different EAE forms are also used as models for the different stages of MS.

Intravenous injection of MSCs in mice with EAE resulted in decreased number of inflammatory infiltrates, fewer demyelinating lesions, and improved neurological function (Zappia, et. al., *Blood* 106: 1755-1761 [2005]; Zhang, et. al., *Exp Neurol* 195: 16-26 [2005]). While some of the peripherally injected cells were found localized paranchemally (Zhang, et. al., *Exp Neurol* 195: 16-26 [2005]), the majority of MSCs were associated with lymphoid organs where they effectively modulate the pathogenic immune response (Zappia, et. al., *Blood* 106: 1755-1761 [2005]; Gerdoni, et. al., *Ann Neural* 61: 219-227 [2007]).

The inventors have demonstrated that injection of mouse MSC-derived neural precursors at the time of EAE onset in mice results in a similar decrease in EAE score compared the studies described above. One million cells were injected either intravenously or intracerebroventriclarly and the mice were followed for 3-4 months. As illustrated in FIG. 5A, there was a decrease in the overall level of disability of mice intravenously injected with MSC-derived neural precursors compared to saline-injected mice. When cells were injected directly into the CNS (FIG. 5B) there was significant delay in onset of EAE as well as decreased overall disability.

Basis for Intrathecal Route of Administration

Preclinical animal models have been used to examine the safety and tolerability of MSCs administered via various routes. Intravenous administration was found to be beneficial in peripheral immune-mediated diseases, such as EAE and graft vs. host disease (GvHD) (Zappia, et. al., *Blood* 106: 1755-1761 [2005]; Bartholomew, et. al., Exp Hematol 30: 42-48 [2002]). MSCs injected intravenously are cleared from the bloodstream after 1 hour (Koc, et. al., *J Clin Oncol* 18: 307.316 [2000]), with the majority of cells being trapped in the lung. It has been estimated that fewer than 1% of i.v. administered MSCs reach the CNS (Corti, et. al., Brain 127: 2518-2532 [2004]), making the intravenous route of administration clinically unfeasible for CNS diseases due to the large number of cells required.

The pathological hallmark of multiple sclerosis is multi-focal, demyelinated lesions in the brain. Lesions with varying degrees of demyelination/remyelination are observed throughout the brain and spinal.cord, although it has been noted that periventricular lesions have a lesser extent of remyelination than deep white matter lesions (Patrikios, et. al., *Brain* 129: 3165-317260 [2006]). Most physical disability in MS is caused by lesions in the spinal cord, thus stem cells could be delivered directly to spinal cord lesions via intraspinal injection. However, such a procedure would require neurosurgery and involves unwarranted risks to the patient. Furthermore, there are typically multiple foci of demyelination that contribute to disability, making it difficult to deliver cells to all of the lesions. In addition, direct injections into CNS tissue would be hazardous and overly aggressive for a non-fatal illness.

The optimal route of delivery should seed MSC-derived neural precursors to the brain and spinal cord via the venous, arterial, or spinal fluid circulation. Intravenous delivery of stem cells is the least invasive route of delivery and has been shown to be safe and tolerable for MSCs. However, IV injection of MSC-derived neural precursors would not guarantee that an adequate number of stem cells penetrate the brain and spinal cord. Therefore, we have selected an intrathecal route of delivery, which is minimally invasive and would seed stem cells into the CNS via cerebrospinal fluid circulation, providing potential access to spinal cord lesions and periventricular brain lesions. Preclinical studies demonstrating the ability of MSCs to migrate toward areas cephalad to that of the injection site (Bakshi, et. al., *J Neurotrama* 23: 55-65 [2006]; Lepore, et. al., *Brain Res* 1045: 206-216 [2005]), suggest that intrathecal administration via lumbar puncture is an effective way of delivering stem cells to areas of CNS injury. Injecting medications or cells into the CSF allows these agents to bypass extra-CNS organs and penetrate the brain rapidly. While the general flow of CSF is rostral to caudal, there is some retrograde CSF flow (Johnson, et. al., *Pharm Res* 22: 1011-1037 [2005]). Several efficacious treatments are administered intrathecally. For example, intrathecal Baclofen (ITB) is used to treat spasticity in ambulatory patients with MS. In a study performed by the inventors, thirty-six patients with severe spasticity were treated with continuous infusion of ITB. Patients were followed from 1 to 13 years. All thirty-six patients had profound loss of spasticity as assessed by the Ashworth scale (Sadiq, et. al., *J Neurol* 253: 563.569 [2006]).

In models of CNS disease, MSCs have been injected intracerebroventricularly (Ohta, et. al., *Exp Neurol* 187: 266-278 [2004]; Amhold, et. al., *Eur J Cell Biol* 85: 551-565 [2006]; Chen, et. al., *J Neurol Sci* 189: 49-57 [2001]) and, in some cases, directly into the pathological CNS tissues (Chopp, et. al., *Neuroreport* 11: 3001-3005 [2000]; Hofstetter, et. el., *Proc Nail Acad Sci USA* 99: 2199-2204 [2002]). While these routes of delivery prove efficacious in animal models, in humans this would translate into a highly invasive and potentially dangerous procedure. MSCs, injected intrathecally into the lumbar region of rats after cervical spinal cord injury, migrated to and accumulated in the area of injury (Bakshi, et. al., *Neurotrauma* 23:55-65 [2006]), demonstrating the validity of this approach. Because of this rostral migration of MSCs, it is inferred that MSCs are sensitive to chemotactic signaling and specific adhesion molecules (Bakshi, Et. al., *J Neurotrauma* 23: 55-56 [2006]; Lapore, et. al., *Brain Res* 1045: 206-216 [2005]). Translated to humans, the intrathecal delivery of stem cells via minimally invasive lumbar puncture may have significant therapeutic potential.

In humans the first issue to be addressed is safety and tolerability. The safest route for cell delivery would be i.v. or intrathecal routes. Based on the preclinical models outlined above, the cells are administered to human subjects cells via lumbar puncture.

In a human trial about to commence, the following procedures and steps will be undertaken to demonstrate the efficacy of administering autologous mesenchymal stem cell-derived neural precursors to humans to treat and/or reduce the severity of MS.

Serum Collection

Bone marrow-derived stem cells were isolated and expanded in autologous serum from the same research subject. The growth of stem cells in autologous serum prevents the introduction of potentially harmful animal products present in fetal bovine serum (Stute, et al. *Exp Hematol* 32: 1212-1225 [2004]). Serum from each research subject is collected prior to the bone marrow aspiration procedure, at the enrollment visit. A health professional collects approximately 200 mL of peripheral blood from each research subject into tubes pre-labeled with the research subject's unique identifier, Patients are then given oral fluids and vital signs taken before being sent home. Blood is immediately transferred to the cell culture laboratory. The blood is then centrifuged, and the serum is collected and pooled using aseptic technique in a biosafety hood, Serum is then filtered through a 0.2 μm filter and then stored in aliquots in a designated −80° C. freezer that is continuously monitored by a freezer monitor with a telephone alert system. Each tube of serum will be labeled with the research subject's unique identifier and the date. Each patient's serum lot will be stored in its own box also labeled with the patient's unique identifier. Materials that may contaminate or adversely affect cellular therapy products will not be stored in this designated freezer. Serum is used to support growth of autologous mesenchymal stem cells.

Bone Marrow Collection

A bone marrow aspiration is performed to obtain a bone marrow aspirate from the posterior iliac crest under sterile conditions following injection of a local anesthetic, Standard bone marrow aspiration procedure is followed using an adult bone marrow kit with a heparinized syringe. For disabled patients who can not be transferred without a Hoyer Lift, the iliac crest is difficult to access. These patients have the bone marrow aspirate obtained from the manubrium of the sternum, at the level of the second intercostal space. This procedure is performed in a wheelchair. Patients whose level of disability prevents them from being able to position themselves so that the hematologist can access the iliac crest will also have the aspirate performed from the sternum. Standard bone marrow aspiration procedure is followed using an adult bone marrow kit with a heparinized syringe. Approximately 10 cc of bone marrow will be aspirated from each patient.

Cell Culture Reagents

A major concern in the literature regarding cell culture reagents in stem cell based therapies is the use of fetal bovine serum (PBS) (Mannello, et. al., *Stem Cells* 25: 1603-1609 [2007]), since bovine serum antigens can remain cell associated causing an immunological reaction, The inventors have eliminated the risks associated with FBS by using autologous serum. Nevertheless, a number of clinical trials have injected MSCs expanded in media supplemented FBS with no significant FBS-associated side effects (Lazarus et. al., *Biol Blood Marrow Transplant* 11: 389-398 [2005]; Le Blanc, et. al., *Lancet* 363: 1439-1441 [2004]; Horwitz, et. al., *Proc Nall Acad Sci USA* 99:8932-8937 [2002]; Bang, et. al., *Ann Neurol* 57: 874-882 [2005]; Mazzini, et al, *Neural Sci* [2007]; Mohyeddin, et. al., *Iran J*

Immunol 4: 50-57 [2007]; Karussis, et. al., *J Neurol Sci* [2007]). One recent study demonstrated that patients transplanted with allogeneic MSCs developed clinically insignificant anti-FBS antibodies and no MSC-specific alloantibodies (Sundin, et, al., *Haematologica* [2007]). In all MSC clinical trials to date, MSCs are expanded in media with FBS and L-Glut, passaged with trypsin, resuspended in either saline or cerebrospinal fluid and delivered intravenously (Lazarus, et. al., *Biol Blood Marrow Transplant* 11: 389-398 [2005]; Le Blanc, et. al., *Lancet* 363: 1439-1441 [2004]; Horwitz, et. al., *Proc Natl Acad Sci USA* 99: 8932-8937 [2002]; Bang, et. al., *Ann Neurol* 57: 874-882 [2005]), intraspinally (Mazzini, et. al., *J Neuro Sci* [2007]), or intrathecally (Mohyeddin, et. al., *Iran J Immunol* 4: 50-57 [2007]; Karussis, et. al., *J Neurol Sci* [2007]), with no significant side-effects associated with infusion, Similar to these trials, the final cell product according to the present invention is thoroughly washed and resuspended in clinical-grade saline prior to human injection to prevent the infusion of cell culture reagents. A general description of all cell culture reagents used in this protocol is outlined herein below.

Basal media: The basal media used to expand MSCs (MSCBM) is manufactured in a regulatory compliant GMP facility at Lonza, The MSCBM is supplemented with Gluta-MAX (Invitrogen), which is a stable dipeptide substitute of L-Glutamine, an essential amino acid required for optimal cell growth. Since Gluta-MAX is metabolized by cells, no infusion-associated toxicity is expected. Indeed, media used to grow MSCs for human infusion is frequently supplemented with L-Glutamine with no apparent side effect (Lazarus et. al., *Biol Blood Marrow Transplant* 11: 389-398 [2005]; Le Blanc, et. al., *Lancet* 363: 1439-1441 [2004]; Horwitz, et. al., *Proc Natl Acad Sci USA* 99:8932-8937 [2002]; Bang, et. al., *Ann Neurol* 57: 874-882 [2005]; Mazzini, et al., *Neural Sci* [2007]; Mohyeddin, et. al., *Iran J Immunol* 4:50-57 [2007]; Karussis, et. al., *J Neural Sci* [2007]). MSCBM is further supplemented with 10% autologous serum. The basal media used to generate MSC-derived neural precursors (NPMM) is also manufactured in a regulatory compliant GMP facility at Lonza. NPMM consists of a basal media (NPBM) with three supplements; 1) recombinant human epidermal growth factor (rhEGF), 2) recombinant human basic fibroblast growth factor (rhbFGF), and 3) neural cell survival factor (NSF-1), EGF and bFGF are each used at a final concentration 20 ng/mL. Stock solutions of EGF and bFGF are provided in a saline solution containing 0.1% bovine serum albumin (BSA) as a carrier protein, which is then diluted to a final concentration of 0.0002% BSA. Mechanistically, EGF and bFGF bind to receptors on the cell surface, and receptor-ligand complexes are then internalized and degraded inside the cell. To ensure complete removal of growth factors prior to injection of MSC-derived neural precursors, the cells are washed thoroughly 3 times in saline. EGF and bFGF levels were tested by ELISA during each washing step and no significant amount of growth factor remained associated with the final cell product. NSF-1 is a propriety formulation used to support the growth of neural progenitor cells. According to Lonza, a component of NSF-1 is of bovine origin. Lonza has stated that all of its bovine-derived products are of USDA-approved origin, thus minimizing possible prion or viral transmission. Stock of NSF-1 is further diluted 50-fold to its working concentration in the basal media.

Trypsin: MSCs are passaged each time with TrypLE (Invitrogen), a microbially produced alternative to animal trypsin. Trypsin is a serine protease found in the digestive system, used to cleave extracellular proteins necessary for cell attachment to the plastic dish. Trypsin is purified from porcine pancreas, whereas TrypLE is manufactured in a controlled fermentation process that is completely free of animal- and human-derived components. Prolonged exposure of trypsin (or TrypLE) leads to cell toxicity and care is taken to minimize exposure of cells to TrypLE, which is added very briefly and then completely washed out. There is no reason to believe that TrypLE serine protease remains associated with the cells, as this would lead to cell toxicity.

Antibiotics: Media is supplemented with an antibiotic-antimicotic solution (Sigma) containing penicillin, streptomycin, and amphotericin B during the initial culture of the mononuclear cell fraction from bone marrow. The antibiotic-antimicotic solution is then omitted from the media at the first cell passage and during all subsequent passages.

MSC Isolation from Bone Marrow

The research subject's sterile bone marrow sample is placed in a pre-labeled bag and immediately transferred from the clinic to the stem cell culture laboratory. All handling of the bone marrow and its derived stem cells is done in a dedicated stem cell processing laboratory under asceptic conditions in a biosafety level 2 laminar flow hood. A research scientist transfers the bone marrow sample to a sterile 50 mL conical tube. Mononucleated cells from the bone marrow sample are isolated by density gradient centrifugation. 10 mL of bone marrow sample is diluted in 20 mL sterile Hank's Balanced Salt Solution (Sigma), layered over 15 mL Ficoll-Paque PREMIUM, endotoxin-free (GE Healthcare, Life Sciences) in a separate sterile conical tube, and centrifuged at 400×g for 40 minutes. The mononucleated cell layer is removed, transferred to a new 50 mL conical, and washed twice by centrifugation at 100×g for 10 minutes in sterile Hank's Balanced Salt Solution. At this time a trypan blue viability assay will be performed and cells will be counted. Cells are placed into a sterile tissue culture flask (75 cm$^2$ T-flask with vented cap) in media consisting of 15 mL MSCBM (Lonza), stable L-Glutamine (GlutaMAX, Invitrogen), and 10% previously collected autologous patient serum, and incubated at 37° C. in a 5% $CO_2$ humidified incubator. An antibiotic-antimicotic solution (Sigma) containing penicillin, streptomycin, and amphotericin B will be added to the media until the first cell passage and then omitted from the media during all subsequent passages. All media formulations are mixed together and filtered through a 0.2 μm filter prior to addition to cells. All media formulations are labeled with the appropriate unique identifier to prevent cross-contamination of reagents.

Expansion of MSCs and Cryopreservation

Culture medium is changed every 3-4 days to remove unattached (hematopoietic) cells. When the initial culture reaches 80% confluency, cells are detached from the surface by enzymatic dissociation using TrypeLE (animal origin free trypsin, Invitrogen), washed in PBS to remove trypsin, and replated into a 150 cm$^2$ T-flask with vented cap with 25 mL media, and labeled passage #1. When passage #1 MSCs reach 80-90% confluency, the cells are trypsinized again (TrypLE), counted, and 300,000 cells are replated into a new 150 cm$^2$ T-flask (cell density 2000 cells/cm$^2$) and labeled passage #2. The remaining cells from passage #1 (approximately 3-9 million cells) are cyropreserved in freezing media containing 10% autologous serum and 10% DMSO. Cells are centrifuged (100×g for 5 minutes) and cell pellet is resuspended in freezing medium at a concentration of 1 million cells per ml. 1 million cells (or 1 ml) is transferred to 2 mL cryovials that are labeled with each research subject's unique identifier. Cryovials are transferred to a dedicated isopropanol freezing container overnight at −80° C., and then stored in liquid nitrogen. Levels of liquid nitrogen are monitored electronically to ensure samples are maintained at an appropriate temperature. When passage #2 MSCs reach 80-90% confluency, 300,000 cells are replated replated into a new 150 cm² T-flask (cell density 2000 cells/cm²) and labeled passage #3, and the remaining cells are cryopreserved. Passage #3 cells are cultured to 80-90% confluency and used for MSC characterization and quality control (see below). 500,000 passage #3 cells will also be collected for gene expression analysis (see "Quality testing of the cells" below). All MSCs used for subsequent expansion, neural precursor selection, and autologous injection are derived from either passage #1 or passage #2 cryopreserved stocks.

Characterization and Quality Control

MSC cultures consist of a heterogenous population of cells, even when generated as single cell-derived colonies (Prockop, et al., *Proc Nall Acad Sci USA* 100 Suppl 1:11917-11923 [2003]). Furthermore, there are no adequate markers specific for MSCs. According to the International Society for Cellular Therapy (Dominici et. al., *Cytotherapy* 8: 315-317 [2006]), the minimal criteria for defining human MSCs include 1) plastic adherence, 2) spindle-shaped morphology, 3) surface antigen expression of ($CD105^+/CD73^+/CD90^+$) and lack of expression of hematopoietic markers ($CD45^-/CD34^-/CD14^-/CD79^-$) and MHC ($HLA-1^-/HLA-DR^-$), and 4) in vitro differentiation into adipocytes, osteoblasts, and chondroblasts. Bone marrow-derived MSCs are evaluated by this set of criteria for each patient. For each set of criteria, patient MSCs are compared to healthy control MSCs from the same passage (purchased from Lonza). Plastic adherence and morphology is evaluated and documented by an Olympus IX71 inverted light microscope connected to a digital camera. Surface antigen expression is evaluated by fluorescent immunocytochemistry, particularly flow cytometry (ED FACS Aria) using FITC (Fluorescein Isothiocyanate)-labeled antibodies against CD105, CD73, CD90, CD45, CD34, CD14, CD79, HLA-I, and HLA-DR (all purchased from BD). Peripheral blood lymphocytes is used as a positive control for hematopoietic markers and Lonza MSCs is used as a positive control for MSCs. Isotype controls is also included. In vitro differentiation of MSCs into adipocytes, osteoblasts, and chondroblasts is carried out using media and methods provided by Lonza, and compared to Lonza MSCs as well as undifferentiated controls. Adipogenic differentiation is qualitatively assessed by Oil Red O staining. The number of Oil Red O positive cells is expected to be 30-100%. Subsequent to osteogenic differentiation, calcium deposition will be quantitated using StanbioTotal Calcium LiquiColor (Stanbio Labs). Expected range of calcium content in a confluent 6-well plate is 10,000-50,000 ng/μl. Chondrogenic differentiation is qualitatively assessed by immunostaining sections of paraffin embedded chondrogenic pellets for Type II collagen, indicative of successful chondroblast differentiation. Patient MSCs must meet all of the above criteria prior to expansion of MSCs for injection and continuation in the study.

Expansion of MSCs from Cryopreserved Stocks

Approximately 1 month prior to stem cell injection, one vial (1 million cells) of passage #1 or passage #2 MSCs from the research subject is removed from liquid nitrogen storage, rapidly thawed, centrifuged to remove DMSO, and immediately plated into a 150 cm² T-flask containing complete medium (MSCBM supplemented with Gluta-MAX and 10% autologous serum). When cells reach 80% confluency, they are passaged exactly as described above into new 150 cm² T-flasks at a density of 2000 cells/cm². Cells are passaged 3-5 times further and expanded to produce up to 50 million cells.

Selection of Neural Precursor Cells from Mesenchymal Stem Cells

MSC-derived neural precursors are selected by detaching the expanded MSCs using TrypLE as described above. 500,000 MSCs are removed for gene expression analysis (see quality testing below), 50,000 cells are re-plated in a 25 cm² T-flask for subsequent karyotype analysis (see quality testing below). Remaining cells are pooled, centrifuged, and resuspended in NPMM media from Lonza (Neural Progenitor Basal Medium, Neural Survival Factor-1, 20 ng/ml EGF, and 20 ng/ml bFGF). Cells are plated at a density of $4-6\times10^4$ cells/cm² in a 75 cm² low-attachment T-flask (BD Falcon) in 15 ml of NPMM. Culture medium is changed every 2-3 days by centrifugation of floating neural precursor clusters, and resuspension in NPMM. MSC-derived neural precursors are cultured-for-10-15-days. Two days prior to injection, 500,000 MSC-derived neural precursors are removed for gene expression analysis.

Quality Testing of the Cells:

Gene expression analysis: Due to the inherent complexity in a biological system compared to a pharmaceutical product, there will be some natural variability in each cell product. Furthermore, the heterogenous nature of MSCs suggests that there will be some variability in gene expression levels between patients. With these caveats in mind, gene expression analysis of each patient's MSCs and MSC-derived neural precursors is performed in order to obtain a quantitative assessment of cell differentiation status as a reflection of each cell product's purity and potency. Samples of 500,000 MSCs (obtained after complete expansion) and 500,000 MSC-derived neural precursors (obtained two days prior to injection date) are stored in RNA Protect (QIAGEN) at −20° C., Each batch of expanded and differentiated MSC and MSC-derived neural precursors is compared to 500,000 MSCs obtained at passage #3 at the time of cryopreservation. One or two days prior to injection date, RNA is extracted using RNA Easy kit (QIAGEN). 1 μg of RNA is used as template for cDNA synthesis (Superscript III, Invitrogen). 2 μl of cDNA template is used as template for real-time quantitative PCR using SyBr green detection (Roche) and previously validated gene-specific primers in a Roche Lightcycler 2.0. A positive control (human brain cDNA) is included in each analysis, which also serves as a batch to batch calibrator, A negative control (no DNA template) is also included each time. A no reverse transcriptase negative control is also included each time to assess for genomic DNA contamination. Samples are analyzed for RNA levels of Nestin (a neural precursor-specific marker), Neurofilament (neuronal marker), GFAP ("glial fibrillary acidic protein", a glial and neural precursor marker) and Vimentin (MSC marker). RPLP (60S acidic ribosomal protein P0) is used as a reference gene, For each sample, the gene:RPLP ratio is determined and compared to the gene:RPLP ratio of the calibrator sample to determine the relative expression level for each gene. In addition, changes in gene expression for each pair of MSC and MSC-derived neural precursor samples is determined as a fold increase or decrease in the relative gene expression level, The inventors have previously determined the relative ratios for each of the above genes in MSCs and MSC-derived neural precursors from 3 patient samples and 1 healthy control sample (Lonza). Nestin increase in MSC-derived neural precursors ranges from 2-4 fold, Neurofilment increase ranges from 5-15 fold, GFAP increase ranges from 7-10 fold, and Vimentin decrease ranges from 0.4-0.7 fold. These quantitative changes in RNA levels correlate with changes in protein expression of these markers (FIG. 8). For each patient, and prior to each injection, MSC and MSC-derived neural precursor pairs will be analyzed for these changes in gene expression levels. MSC-derived neural precursors that fail to show gene expression changes within the expected range is discarded and not injected. In this case, MSCs expansion and MSC-derived neural precursor induction is repeated starting from another cryopreserved stock. Should the MSC-derived neural precursors fail quality testing a second time, the patient is removed from the study.

Sterility testing: 1-2 days prior to injection of autologous stem cells, cell conditioned media is tested by PCR for trace levels of contamination. The PCR test sensitively detects mycoplasma and eubacteria contamination of the culture. VenorGeM Mycoplasma Detection Kit is purchased from Sigma, and OnarEUB Eubacteria Detection Kit is purchased from Minerva Biolabs, Each PCR test is carried out by a trained molecular biologist at the MSRCNY. Quality testing by PCR will include both positive and negative controls according to manufacturer's instructions. Any samples confirmed positive for contamination will be discarded and not used for injection, and the source of contamination will be investigated. Possible sources of contamination include cell culture reagents, $CO_2$ incubator, contamination of laminar flow hood, and improper technique. All reagents suspected as a source of contamination are discarded, and all equipment will be cleaned. All MSC-derived neural precursors are confirmed negative for contamination by PCR prior to injection into any research subject. At the same time as PCR analysis, each sample of conditioned media is sent to an outsourced company (Clongen Laboratories, LLC) for sterility testing via culture method. In the event that a positive result is seen, the source of infection will be methodically investigated, In addition, the patient will be re-evaluated for signs of infection. The patient will have a CBC with diff. If the patient does not show signs of infection a lumbar puncture will not be performed because of the risks of the procedure.

Karyotype analysis: A sample of MSCs grown in a 25 cm² T-flask (replated after complete expansion) is subjected to karyotype analysis to test for any chromosome abnormalities that may arise during ex vivo expansion. The frequency of chromosomal aberrations during ex vivo expansion of mesenchymal stem cells has been shown to be very low, occurring only in late passage cells (Rubio, et. al., *Cancer Res* 65: 3035-3039 [2005]). The mesenchymal stem cells used in this protocol will all be early passage cells with total ex vivo culture time between 1 and 2 months, which is well within the time period where they can be managed safely (Rubio, et. al., Cancer Res 65: 3035-3039 [2005]). Results from karyotype analysis is obtained prior to injection of MSC-derived neural precursors. Should any karyotype abnormality be determined in the expanded MSCs, the corresponding MSC-derived neural precursors is discarded and not injected.

EXPERIMENTAL

Nestin Protein Expression in MSC-derived Neural Precursors

Nestin protein expression was determined by standard immunofluorescence. Cells were fixed in 4% paraformaldehyde and labeled with Nestin antibody (Chemicon) followed by anti-rabbit secondary antibody conjugated to Alexa-594 (Molecular Probes). FIG. 6 illustrates the increased nestin expression in MSC-derived neural precursors. The neural precursors in panel B were derived from MSCs after culturing in Neural Progenitor Maintenance Media (NPMM). Panels A-C of FIG. 6 was viewed at 100× magnification and panel D was viewed at 200× magnification.

Changes in Gene Expression of Neural Precursor Cells from MSCs

MSC culture was expanded in mesenchymal stem cell growth medium (MSCGM) for 4 passages. MSC-NPs were selected from MSCs by culturing for 15 days in NPMM, Cells were plated in PDL/Laminin-coated 8-well slides and assayed 18 hours later for protein expression by standard immunofluorescence. Cells were immunolabeled with antibodies against Nestin (1:2000), GFAP (1:500), Neurofilament-M (NF-M, 1:1000), Vimentin (1:5000), alpha smooth muscle isoform of actin (actin αSM, 1:1000), all purchased from Chemicon. Secondary antibodies against mouse IgG or rabbit IgG conjugated to Alexa-594 were from Molecular Probes, Secondary antibody alone was included as a control, Labeled cells were mounted with DAPI and viewed with an Olympus BX60 fluorescent microscope under 200× magnification. The increased protein expression of nestin, GFAP, and neurofilament-M, and decreased expression of Vimentin and αSM actin in MSC-derived neural precursors compared to MSCs is shown in FIGS. 7 and 8.

In Vitro Differentiation of MSC-derived Neural Precursors

MSC-NPs were differentiated into neuronal and oligodendroglial cell types in vitro. MSC-NPs were selected from MSCs by culturing for 15 days in NPMM. Cells were plated in matrigel-coated 8-well slides and cultured in either basic medium alone (control), or containing 100 ng/ml bFGF for 21 days. Cells were fixed in 4% paraformaldehyde and immunolabeled with primary antibodies against class III β-tubulin (1:100), microtubule associated protein-2 (MAP-2, 1:100), oligodendrocyte marker O4 (1:200), oligodendrocyte marker O1(1:1000), Galactocerebroside (GalC, 1:50), and Nestin (1:1000), all from Chemicon, Fluorescently conjugated secondary antibodies against mouse IgG or IgM (Alexa594) or rabbit IgG (Alexa-488) were from Molecular Probes. Labeled cells were mounted with DAPI and viewed with an Olympus BX60 fluorescent microscope under 200X magnification. FIGS. 1 and 2 illustrate the increased neuronal and oligodendroglial marker expression in MSC-derived neural precursors (MSC-NP) and MSCs after in vitro differentiation.

Anti-inflammatory Characteristics of MSC-derived Neural Progenitors

CFSE-labeled allogeneic T cells from peripheral blood were stimulated with PHA (Phytohemagglutinin) for 4 days. T cells were cultured alone, or co-cultured with human MSCs from donor 1) or MSC-derived neural precursors from donor 1 and from donor 1 T cells proliferation was measured by FACS analysis based on decreased CFSE fluorescence of CD3+ cells. The anti-inflammatory display of the MSC-derived neural precursors is illustrated in FIG. 3.

MSC-derived Neural Precursors Loss of Differentiation Capacity

For adipogenic induction, MSCs or MSC-NPs were cultured in either MSCGM (control) or adipocyte induction media containing insulin, dexamethasone, indomethacin, and IBMX for 3 weeks. Cells were fixed and lipid vacuoles were stained with Oil Red O. For osteogenic induction, MSCs or MSC-NPs were cultured in either MSCGM (control) or osteocyte induction media containing dexamethasone, ascorbic acid, and β-glycerophosphate for 3 weeks. Total calcium deposition was assayed by Calcium (CPC) Liquicolor kit (Stanbio Laboratory). The loss In capacity of the MSC-derived neural precursors to differentiate into mesodermal lineages is shown in FIG. 4.

Preparation of Autologous Stem Cells for Injection

Prior to injection, MSC-derived neural precursors are pooled and collected by centrifugation. Cell clusters are broken up into a single cell suspension by incubation with TrypLE for 5 minutes at room temperature. Cells are washed three times in sterile, injection grade 0.9% Sodium Chloride, USP to remove any traces of media and growth factors. A total of 10 million cells are resuspended in 0.2 ml of sterile, injection grade 0.9% Sodium Chloride USP, transferred to a small sterile tube, and placed into a labeled, sterile container for transport to the IMSMP. 10 million cells is a relatively low dose of cells and was calculated using averages from animal and human trials.

Injection of Autologous Stem Cells

Patients received intrathecal injections of the isolated and expanded stem cells under sterile conditions following standard procedure. A sterilized LP tray was used. A sterile field was established, and 1% lidocaine was used as a local anesthetic. The primary investigator aspirated 6 mL of CSF at the L3-L4 level using a 25 gauge needle. A standard LP kit has a 20 gauge needle however in this study a 25 gauge needle will be used to lower the incidence of headaches associated with spinal taps, If access is limited at the L3-L4 level, the L2-L3 level will be used as an alternative site. The stem cells are added to 3 mL of CSF, and the CSF and stem cell mixture is injected intrathecally, and then chased by an additional 3 mL of CSF. This procedure takes approximately 30 minutes. Immediately following this procedure, the patient is infused with 80 mgs of Tobromycin and 500 mgs of Vancomycin (McKesson Corporations). This infusion takes approximately four hours, Vancomycin is the drug of choice for *S. epidermidis*, which would be a contaminant from the skin during the lumbar puncture procedure. It is also the drug used to treat penicillin resistant *S. pneumoniae*. Vancomycin is also indicated in empiric use in meningitis until an organism has been identified. Tobromycin is synergistic with Vancomycin and is also the treatment of choice for pseudomonas infections. Also Vancomycin and Tobramycin are indicated in empiric use to treat meningitis in all neurosurgical procedures at most intuitions (The Manual of Medical Therapeutics, 30$^{th}$ Edition). Injections occur every three months and patients undergo three rounds of treatment. The treatment phase of this study will take 9 months and patients will be followed for 12 months after the third (final) treatment, This is an adequate amount of time for cells to integrate and for any problems with safety and tolerability to become apparent.

Dosing Schedule for Humans

Autologous stem cell injections occur at three month intervals over the course of nine months. 10 million MSC-derived neural precursors will be injected at each treatment, This dose was calculated based on preclinical safety data where $2.5 \times 10^6$ (Black, et. al., *Blood Cells Mol Dis* 27: 632-636) cells bone marrow-derived MSCs were engrafted into the CNS of healthy rhesus macaques with no adverse effects evaluated over a 6-month period (Isakova, et. al., *Mol Ther* 13: 1173-1184 [2006]). The HED (http://www.fda.gov/cber/gdlns/dose.htm) was calculated to be $1.5 \times 10^5$ (Woodbury; et. al., *J Neurosci Res* 69: 908-917) cells/kg or approximately 10 million cells per patient. This dose was safe and well tolerated in the MS clinical trial conducted in Iran (Mohyeddin, et. al., *Iran J Immunol* 4: 50-57 [2007]). Patients received intrathecal injections of 2.5 million to 13 million MSCs. A dose of ten million cells is also considered a low dose compared to intraspinal delivery of MSCs in the ALS trial (ranged 7-150 million cells) (Mazzini, et. al., *Neurol Res* 28: 523-526 [2006]). Preclinical studies have concluded that a low dose of cells injected multiple times is more effective than single high dose injections (Bakshi, et. al., *J Neurotrama* 23: 55-65 [2006]; Lepore, et. al., *Brain Res* 1045: 206-216 [2005]), which is consistent with our study design. Immediately following cell infusion, patients will also receive an infusion of 80 mgs of Tobromycin and 500 mgs of Vancomycin. This medication will be supplied by McKesson Corporation.

The cells are manufactured following all Good Manufacturing Practice regulations. Cells are cryopreserved in media containing 10% autologous serum and 10% DMSO in 2 ml cryovials. Cryovials are labeled with each research subject's unique identifier and stored in liquid nitrogen, with each serum lot stored in a separately labeled box. Storage location for each sample is recorded in a database, which is backed up by hardcopy.

Levels of liquid nitrogen are monitored electronically to ensure samples are maintained at an appropriate temperature. All mesenchymal stem cells used for subsequent expansion, neural precursor selection, and autologous injection are derived from cryopreserved stocks. There is no evidence that cells stored in liquid nitrogen in an undisturbed manner lose either in vitro determined viability or biological activity. Therefore, no expiration date need be assigned to MSCs stored continuously in liquid nitrogen. Approximately 1 month prior to stem cell injection, mesenchymal stem cells from the research subject are removed from liquid nitrogen storage and expanded in Mesenchymal Stem Cell Basal Medium containing autologous serum, as described above. Cells are passaged 3-5 times in tissue culture flasks and expanded to produce 50 million cells. MSCs are subsequently cultured in Neural Progenitor Maintenance Medium for 10-15 days to generate MSC-derived neural precursors.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for treating multiple sclerosis in a human patient, comprising administering a population of neural precursors to the patient, wherein said population of neural precursors is derived by a process comprising the steps of (a) expanding a population of autologous mesenchymal stem cells from the patient in growth serum comprising autologous serum; (b) culturing the expanded population of mesenchymal stem cells in a neural progenitor basal medium (NPBM) supplemented with epidermal growth factor (EGF), basic fibroblast growth factor (bFGF), and neural cell survival factor-1 (NSF-1), and (c) collecting floating cell clusters from the NPBM-cultured cells, thereby obtaining said population of neural precursors, and wherein said population of neural precursors has increased expression of nestin, glial fibrillary acidic protein (GFAP), and neurofilament-M (NF-M), and decreased expression of alpha smooth muscle (αSM) actin, relative to the expression of nestin, GFAP, NF-M, and αSM actin in the population of mesenchymal stem cells from which the population of neural precursors is derived.

2. The method of claim 1, wherein the population of mesenchymal stem cells is collected from the bone marrow of said patient.

3. The method of claim 1, wherein the process further comprising the steps of (d) measuring in a test portion of the collected cells, expression of nestin, GFAP, NF-M, and αSM actin, relative to the expression of nestin, GFAP, NF-M, and αSM actin in a test portion of the mesenchymal stem cells expanded in step (a), and (e) selecting the remaining portion of the collected cells as said population of neural precursors for administration to the patient based on increased expression of nestin, GFAP, and NF-M, and decreased expression of αSM actin on a population basis in said test portion of the collected cells, relative to the expression of nestin, GFAP, NF-M, and αSM actin in said test portion of mesenchymal stem cells.

4. The method of claim 3, wherein another portion of said neural precursors is tested for sterility and chromosomal abnormalities prior to administration to the patient.

5. The method of claim 1, wherein a portion of said mesenchymal stem cells are tested for sterility, viability, and expression of one or more of: CD105, CD73, CD90, CD45, CD34, CD14, CD79, and HLA-DR, prior to expansion of said mesenchymal stem cells.

6. The method of claim 1, wherein said neural precursors are administered by intrathecal injection.

7. The method of claim 6, wherein the neural precursor cells are administered intrathecally by lumbar puncture.

8. The method of claim 1, wherein said neural precursors are administered at three-month intervals over a course of nine months.

9. The method of claim 8, wherein approximately 10 million neural precursors are injected at each administration.

10. The method of claim 1, wherein the neural precursors are administered in autologous cerebrospinal fluid.

11. The method of claim 1, further comprising collecting autologous serum from said patient, prior to collecting said mesenchymal stem cells.

* * * * *